(12) United States Patent
Green et al.

(10) Patent No.: US 11,986,822 B2
(45) Date of Patent: May 21, 2024

(54) MICRODEVICE FOR DIFFERENTIAL SEPARATION, PURIFICATION AND AMPLIFICATION OF FORENSIC SAMPLES

(71) Applicant: VIRGINIA COMMONWEALTH UNIVERSITY, Richmond, VA (US)

(72) Inventors: Tracey Dawson Green, Glen Allen, VA (US); James Landers, Charlottesville, VA (US)

(73) Assignees: Virginia Commonwealth University, Richmond, VA (US); University of Virginia Patent Foundation, Charlottesville, VA (US)

(*) Notice: Subject to any disclaimer, the term of this patent is extended or adjusted under 35 U.S.C. 154(b) by 660 days.

(21) Appl. No.: 16/484,142

(22) PCT Filed: Feb. 7, 2018

(86) PCT No.: PCT/US2018/017213
§ 371 (c)(1),
(2) Date: Aug. 7, 2019

(87) PCT Pub. No.: WO2018/148271
PCT Pub. Date: Aug. 16, 2018

(65) Prior Publication Data
US 2020/0023366 A1    Jan. 23, 2020

Related U.S. Application Data

(60) Provisional application No. 62/455,691, filed on Feb. 7, 2017.

(51) Int. Cl.
*B01L 3/00*    (2006.01)
*B01L 7/00*    (2006.01)
*C12Q 1/686*   (2018.01)

(52) U.S. Cl.
CPC ..... *B01L 3/502761* (2013.01); *B01L 3/50273* (2013.01); *B01L 7/52* (2013.01);
(Continued)

(58) Field of Classification Search
None
See application file for complete search history.

(56) References Cited

U.S. PATENT DOCUMENTS 5,587,128 A * 12/1996 Wilding ................. C12Q 1/686
                                                435/6.12
2005/0069913 A1 * 3/2005 Mian ..................... F16K 99/003
                                                435/6.16
(Continued)

FOREIGN PATENT DOCUMENTS

WO  WO 2016/209900    * 12/2016  .......... G01N 33/543
WO     2017/019768 A1    2/2017
WO  WO 2017/019768    *  2/2017  .............. B01J 14/00

*Primary Examiner* — Robert T. Crow
(74) *Attorney, Agent, or Firm* — WC&F IP

(57) ABSTRACT

Microfluidic devices for analyzing cellular components from biological samples which contain more than one cell type are provided. The microdevice separates cells by type, releases cellular components such as DNA (e.g. by cell lysis) and processes the cellular components (for example, by amplification) to generate products of interest for further analysis. Samples that can be analyzed using the microfluidic devices include forensic samples such as samples from sexual assault victims, and the products of interest include short tandem repeat (STR) amplicons for DNA profiling.

16 Claims, 13 Drawing Sheets

(52) U.S. Cl.
CPC ...... *C12Q 1/686* (2013.01); *B01L 2200/0605* (2013.01); *B01L 2300/0636* (2013.01); *B01L 2300/087* (2013.01); *B01L 2300/0883* (2013.01); *B01L 2300/1822* (2013.01); *B01L 2300/1894* (2013.01); *B01L 2400/0409* (2013.01); *B01L 2400/06* (2013.01)

(56) References Cited

U.S. PATENT DOCUMENTS

| | | | |
|---|---|---|---|
| 2009/0298059 A1* | 12/2009 | Gumbrecht | G01N 35/00732 435/287.2 |
| 2013/0004956 A1* | 1/2013 | Landers et al. | C12M 1/34 |
| 2013/0295602 A1* | 11/2013 | Fowler et al. | C12Q 1/68 |
| 2014/0134631 A1 | 5/2014 | Clime et al. | |
| 2015/0260710 A1* | 9/2015 | Tseng | G01N 33/545 506/13 |

* cited by examiner

MICRODEVICE FOR DIFFERENTIAL SEPARATION, PURIFICATION AND AMPLIFICATION OF FORENSIC SAMPLES

CROSS-REFERENCE TO RELATED APPLICATIONS

This application claims benefit of U.S. provisional patent application 62/455,691, filed Feb. 7, 2017, the complete contents of which are hereby incorporated by reference.

BACKGROUND OF THE INVENTION

Field of the Invention

The invention generally relates to a microfluidic device for analyzing cellular components from biological samples which contain more than one cell type. In particular, some embodiments involve differential separation, purification, and amplification of forensic samples.

Background

The field of microfluidics employs devices capable of reducing the amount of time, reagents, and space required to perform scientific processes. To that end, micro total analysis systems (µTAS), often described as a "lab-on-a-chip", have been developed, especially single use devices made of plastics. Fields in which such devices have achieved importance include those which involve analysis of nucleic acids such as DNA.

Microdevices have many advantages over traditional, manual DNA analysis methods, such as lower cost, the use of smaller volumes of each reagents and fast processing times. In addition, microdevices are typically closed systems with no tube transfers. This eliminates the risk of contamination from sample-to-sample or examiner-to-sample.

Microdevices should offer great benefits to the field of forensic DNA analysis, especially for analysis of sexual assault samples which take significantly longer to process than other forensic samples due to the manual, tedious bench procedures as well as lengthy, complex mixture interpretation that is often inevitable, as these samples usually contain DNA from multiple contributors. Some attempts have been made to improve this process by incorporating modern technologies, but the art is in need of alternatives which are cost effective and can be readily incorporated into the work flow of a typical analytical lab.

SUMMARY OF THE INVENTION

Other features and advantages of the present invention will be set forth in the description of invention that follows, and in part will be apparent from the description or may be learned by practice of the invention. The invention may be realized and attained by the devices, compositions, and methods particularly pointed out in the written description and claims hereof.

The invention relates to an analytical system comprising a microdevice for the rapid, low-cost processing of biological samples comprising cells of more than one type. The simple, inexpensive microdevice replaces some of the most laborious steps of processing mixed cell samples by integrating on-chip modules for differential separation of cells by type and a rotational platform for microfluidic control within the device. Differential cell separation is accomplished by utilizing capture molecules (such as those containing antibodies) that are specific for a cell type. Once captured, cell components, including DNA, are purified and processed on chip. Centrifugal force is applied to effect movement, through the device, of cells and cell components in various stages of processing. Ultimately, the microdevice advantageously produces, within minutes or hours, a sample of a cellular component such as nucleic acid (e.g. DNA) and, optionally, a sample of products generated from the cellular component (e.g. amplicons such as short tandem repeats (STRs) generated from DNA by polymerase chain reaction (PCR)).

In some aspects, the sample containing a mixture of cell types is a forensic sample, such as a sexual assault sample and the cell types in the sample include those of a victim and those of an alleged perpetrator, e.g. typically at least epithelial cells of the victim and sperm cells of the perpetrator. In such aspects, an exemplary microdevice ultimately provides a DNA sample for storage and/or further analysis, as needed, and amplified short tandem repeat (STR) products for off-line processing and analysis by traditional amplicon separation/detection (e.g. via capillary electrophoresis), quantitation, comparison to databases, etc. Exemplary microdevices thus provide a much needed means to rapidly and cost-effectively decrease the growing backlog of untested sexual assault samples.

It is an object of this invention to provide a microfluidic device, comprising an on-chip differential separating chamber configured to receive a biological sample; capture molecules affixed to a substrate in the on-chip differential separating chamber, wherein the capture molecules are capable of specifically or selectively sequestering a cell type of interest from the biological sample; and at least one microvalve openable during application of a centrifugal force, wherein the at least one microvalve is configured i) to prevent egress of the capture molecules affixed to the substrate and any cells sequestered by the capture molecules, and ii) to allow egress of at least some components of the biological sample which are unsequestered by the capture molecules. In some aspects, the microfluidic device further comprises a sample-input chamber configured for separating the biological sample from a sample collection device, wherein the on-chip differential separating chamber is downstream of the sample-input chamber. In some aspects, the microvalve is a passive burst valve which opens under the influence of the centrifugal force. In further aspects, the configuration of the microvalve to perform selective prevention and allowance of egress is on the basis of size, wherein a smaller size of the microvalve as compared to the substrate prevents egress of the substrate. In additional aspects, the microfluidic device further comprises a lysis chamber downstream of the microvalve and configured for combining a lysis solution with the at least some components of the biological sample which are unsequestered by the capture molecules. In some aspects, the on-chip differential separating chamber is configured to receive and contain a separate lysis solution. In yet further aspects, the microfluidic further comprises i) a first metering chamber downstream from the on-chip differential separating chamber, and ii) a second metering chamber downstream from both the on-chip differential separating chamber and the lysis chamber, wherein the first and second metering chambers are parallel circuit elements with respect to one another. In additional aspects, the microfluidic device further comprises i) a first storage chamber downstream of the first metering chamber; ii) a second storage chamber downstream of the second metering chamber; iii) a first reagent mixing chamber downstream of the first metering chamber and in parallel with the first storage chamber; and iv) a second reagent mixing chamber downstream of the second metering chamber and in parallel with the second storage chamber. In other aspects, the microfluidic device further comprises a first infrared (IR) polymerase chain reaction (PCR) chamber and a second IR PCR chamber downstream from the first mixing chamber and the second mixing chamber, respectively, configured for combining cellular materials and PCR reagents. In further aspects, the first and second metering chambers are connected to the first and second IR PCR chambers, respectively, via a first serpentine mixing channel and a second serpentine mixing channel, respectively. In other aspects, the microfluidic further comprises one or more vents which allow access to one or more of the first chamber, the second chamber, the third chamber, the first metering chamber, the second metering chamber, the first storage chamber, the second storage chamber, the first IR PCR chamber and the second IR PCR chamber. In additional aspects, the microfluidic device further comprises an IR PCR reference chamber. In other additional aspects, the IR PCR reference chamber comprises a thermocouple. In some aspects, the capture molecules are antibodies. In other aspects, the antibodies are anti-sperm antibodies.

The invention also provides a microfluidic method, comprising combining a biological sample and capture molecules affixed to a substrate in an on-chip differential separating chamber; by the capture molecules, specifically or selectively sequestering a cell type of interest from the biological sample; opening at least one microvalve during application of a centrifugal force; with the at least one microvalve, preventing egress of the capture molecules affixed to the substrate and any cells sequestered by the capture molecules, and allowing egress of at least some components of the biological sample which are unsequestered by the capture molecules. In some aspects, the microfluidic method further comprises separating the biological sample from a sample collection device in a sample-input chamber before receiving the biological sample in the on-chip differential separating chamber. In some aspects, the microvalve is opened under the influence of the centrifugal force. In further aspects, the steps of preventing and allowing egress are performed on the basis of size, wherein a smaller size of the microvalve as compared to the substrate prevents egress of the substrate. In yet further aspects, the microfluidic method of claim 16, further comprises lysing the at least some components of the biological sample which are unsequestered by the capture molecules in a lysis chamber downstream of the microvalve. In additional aspects, the microfluidic method further comprises lysing at least some cells sequestered by the capture molecules in the on-chip differential separating chamber. In other aspects, the microfluidic method further comprises receiving cellular components in a first metering chamber downstream of the on-chip differential separating chamber, and receiving other cellular components in a second metering chamber downstream of both the on-chip separating chamber and the lysis chamber, wherein the first and second receiving steps are conducted in parallel with respect to one another. In additional aspects, the microfluidic method further comprises i) releasing from the first metering chamber a first portion of the cellular components to a first storage chamber via a mechanical valve, and a second portion of the cellular components to a first reagent mixing chamber via a burst valve openable upon application of a centrifugal force; ii) releasing from the second metering chamber a first portion of the other cellular components to a second storage chamber via a mechanical valve, and a second portion of the other cellular components to a second reagent mixing chamber via a burst valve openable upon application of a centrifugal force, wherein the first and second releasing steps are conducted in parallel with respect to one another. In further aspects, the microfluidic method further comprises receiving in a first infrared (IR) polymerase chain reaction (PCR) chamber downstream of the first mixing chamber a cellular material and PCR reagents, receiving in a second IR PCR chamber downstream of the second mixing chamber a cellular material and further PCR reagents, generating amplicons by PCR amplification in the first and second IR PCR chambers, and retrieving the amplicons. In certain aspects, flow from the first and second metering chambers to the first and second IR PCR chambers, respectively, is conducted via a first serpentine mixing channel and a second serpentine mixing channel, respectively. In other aspects, the microfluidic method further comprises accessing by one or more vents one or more of the first chamber, the second chamber, the third chamber, the first metering chamber, the second metering chamber, the first storage chamber, the second storage chamber, the first IR PCR chamber, and the second IR PCR chamber. In yet further aspects, the microfluidic method further comprises referencing an IR PCR reference chamber. In some aspects, the IR PCR reference chamber comprises a thermocouple. In additional aspects, the biological sample is a sample from a sexual assault victim. In some aspects, the amplicons are short tandem repeat (STR) amplicons. In additional aspects, the capture molecules are antibodies. In yet further aspects, the antibodies are anti-sperm antibodies.

The invention also provides a rotational microfluidic platform system, comprising: a microfluidic device as set forth above, a heater, a cooler, a centrifugal force (CF) source, wherein the microfluidic device is attachable to the CF source. In some aspects, the heater is an infrared (IR) lamp. In other aspects, the cooler is a fan. In additional aspects, the CF source is a centrifuge platform. In yet further aspects, the rotational microfluidic platform system comprises a controller configured to control the heater, cooler, and CF source. In other aspects, the controller comprises one or more computers.

The invention also provides a method for amplifying, by polymerase chain reaction (PCR), sperm cell DNA from a sample, comprising: i) introducing the sample into a microdevice as set forth in claim 1; ii) within the microdevice: separating sperm cells from non-sperm cells, lysing sperm cells to release DNA, and generating amplicons by PCR amplification of DNA released in the lysing step; and iii) retrieving the amplicons from the microdevice. In certain aspects, the sample is a sample from a sexual assault victim. In additional aspects, the amplicons are short tandem repeat (STR) amplicons.

The invention also provides a microfluidic device for conducting polymerase chain reaction (PCR) amplification of DNA, comprising (I) a first chamber for receiving a biological sample; (II) a second chamber configured to receive the biological sample from the first chamber, wherein i) the second chamber comprises capture molecules capable of specifically or selectively sequestering a cell of interest from the biological sample, the capture molecules being affixed to a substrate; ii) the second chamber comprises a burst valve openable upon application of centrifugal force to the microdevice, wherein a size of the burst valve allows sample components to egress the second chamber and enter a third chamber configured to receive and contain a lysis solution, but is insufficient to allow the capture molecule affixed to the substrate to pass through; and iii) the second chamber is configured to receive and contain a lysis solution; (III) a first metering chamber configured to receive cellular components from the second chamber and a second metering chamber configured to receive cellular components from the third chamber, wherein the first and second metering chambers are configured to (a) release a first portion of the cellular components to a first storage chamber and a second storage chamber, respectively, via a mechanical valve; and (b) release a second portion of the cellular components to a first reagent mixing chamber and a second reagent mixing chamber, respectively, via a burst valve openable upon application of centrifugal force to the microdevice; and (IV) a first infrared (IR) PCR chamber and a second IR PCR chamber configured to receive and contain cellular material from the first mixing chamber and the second mixing chamber, respectively, and PCR reagents.

DETAILED DESCRIPTION

Figure 1A:
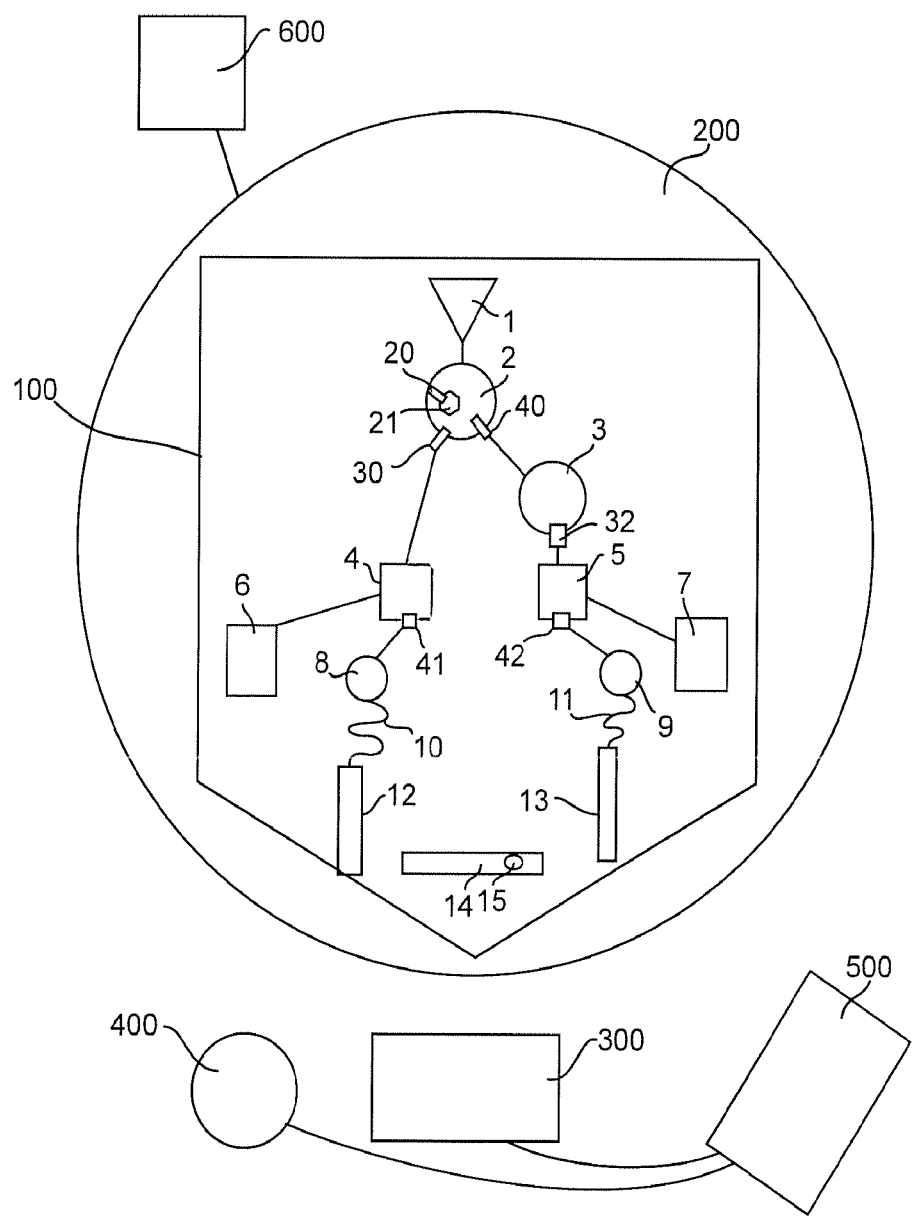
FIGS. 1A and B. Schematic representation of A, an exemplary microdevice and system; and B, representative immobilized capture molecule.

In some aspects, what is provided is a system comprising an improved single-use (disposable), multi-compartment, microfluidic device for analyzing cellular components such as nucleic acids (e.g. DNA) from biological samples which contain, or which are suspected of containing, more than one cell type. The microdevice separates cells by type, releases cellular components (such as DNA) and processes the cellular components (e.g by amplification) to generate products of interest for further analysis. The system comprises at least a microfluidic device or "microdevice" as described herein; a source of centrifugal force, the microdevice being operably attachable to the source of centrifugal force; and at least one heat source (i.e. a heater) that is capable of providing intermittent heat to one or more sections of the microdevice in a controlled manner. Systems also typically include a cooling source (i.e. a cooler)(e.g. a fan), and a controller (e.g. one or more computers) capable of (e.g. programmed to) control operation and coordination of the system elements. Methods of using the system and/or the microdevice to analyze biological samples containing, or suspected of containing, a plurality (e.g. two or more, or at least two, etc.) types of cells are also provided.

Overview of the Invention

Some exemplary embodiments comprise, consist of, or otherwise involve microfluidic devices (sometimes referred to as "microdevices" for brevity). An exemplary microdevice may comprise or consist of a chip, e.g. a lab-on-a-chip (LOC). An exemplary microdevice may generally comprise one or more chambers, one or more conduits (e.g. channels) for establishing fluid communication between or among chambers, and one or more valves (e.g. microvalves) for regulating egress from and ingress to chambers and/or the passage and blockage of flow within conduits and channels.

"Chamber(s)" as used herein may be interchangeably referred to as "compartment(s)". Generally, these may be spaces within a unitary microdevice and typically (but not necessarily) have fixed spatial relationships to one another by virtue of being part of the same unitary device or structure. For instance, a microdevice may have a unitary body of respective cavities which form chambers. Chambers of a chip device or chip system may be described as "on-chip". Processes carried out by or in such chambers may also be described as "on-chip". Chambers and conduits are generally spaces defined by one or more walls or other barriers to have a fixed or substantially fixed geometry and volume. The space or spaces of chambers and conduits may be filled (permanently or temporarily, partially or completely) by matter which may move between chambers when desired and permitted.

A chamber generally comprises a sufficient number of boundaries (e.g., walls) to partially or fully enclose a space. A chamber which is configured to retain matter (e.g., prevent egress of the matter), be it temporarily or permanently, may be described as enclosing the matter to be retained. Matter may exit a chamber via a conduit, a valve, a vent, or other opening, if such is provided. In the case of microdevices, chambers and conduits are frequently but not necessarily isolated from direct contamination by environmental agents outside the microdevice. In some instances a chamber or conduit may be hermetically sealed or substantially hermetically sealed with respect to external contaminants (noting that test samples and constituents thereof are not regarded as contaminants in the sense that they may be deliberately introduced into a chamber or conduit).

Chambers may be referred to as upstream or downstream of one another. As between two chambers, where matter moves from the first chamber to the second chamber, the first chamber is "upstream" of the second chamber. Conversely, the second chamber is "downstream" of the first chamber. This characterization is applicable when matter moves directly from the first chamber to the second chamber, and it remains applicable even if further chambers, channels, or valves intervene in the flowpath between the first and second chambers. For example, the expression "a sample moves from a first chamber to a second chamber which is downstream of the first chamber" permits but does not require the possibility of the sample moving through one or more further chambers, conduits, valves, etc. before it reaches the second chamber. By contrast, the expression "a sample moves from a first chamber directly to a second chamber which is downstream of the first chamber" may be used to indicate that no chambers intervene the flowpath between the first and second chambers. Naturally, at least a conduit may exist between the first and second chambers to place them in fluid communication. Alternatively, if the chambers are immediately adjacent to one another, it may be that a valve without any accompanying conduit is sufficient to fluidically connect the two chambers.

Chambers may form circuits, e.g. fluid circuits, and be arranged in a particular sequence or sequences. Like electrical circuit elements, fluid circuit elements may be arranged in series or in parallel. If two circuit elements (e.g., two chambers) are arranged in parallel, matter which passes through one of the chambers cannot also pass through the other of two chambers. In short, two elements in parallel are neither upstream nor downstream of one another, as each belongs to a separate flowpath. By contrast, circuit elements which are in series are by definition part of the same flowpath, and one is necessarily upstream or downstream of the other. Changes in valve states (e.g. open to closed or closed to open) may alter flowpaths in a microdevice such that the relationships of respective chambers (e.g. parallel configuration or series configuration) are subject to change based on the valve states.

In some aspects, the samples that are analyzed by the microdevices described herein comprise, or are reasonably thought to comprise, more than one type of cell. Accordingly, at least one of the types of cells in a sample to be analyzed using an exemplary disclosed microdevice is differentially selectable from other cells types in the sample, and, when introduced into a compartment of the device, is "captured" e.g. by selective or specific binding to a capture molecule such as an antibody which is immobilized on a support substrate. In some aspects, unbound cells are separated from cells bound to the support substrate via the use of a valve, e.g. a microvalve, e.g. a burst valve, which opens upon application of centrifugal force. When open, the burst valve opening is too small to allow the support to pass through and bound cells are thus left behind in the compartment. Once separated, the cells of interest and unbound cells (in separate compartments) are simultaneously treated "side-by-side" in parallel (e.g. by lysing) to release the cellular components thereof, e.g. nucleic acids such as DNA. The released components of the bound and unbound cells are then (separately) each transferred to another chamber of the device (e.g. by centrifugal force through a valve) for further processing. For example, for DNA, a portion of each sample (bound and unbound) undergoes amplification of short tandem repeats (STRs) via polymerase chain reaction (PCR), thereby providing PCR products whose characteristics are specific for each individual human, to a high degree of probability. In this case, the amplified STRs and an unprocessed, unamplified portion of each DNA sample (bound and unbound) are subsequently retrieved from the device and provided to an analyst for storage and/or further analysis as needed e.g. quantitation, comparison of results to one or more databases, additional sequencing or characterization, etc. It is noted that analysis of the cellular components of unbound cells serves as an internal control for purity of the bound cells of interest, and also to confirm the identity of, e.g. either a victim or suspect in a forensic case. The identity of the unbound cells depends on which cell fraction is targeted with a particular capture molecule. For example, if the epithelial fraction of a sperm containing sample is targeted, then the unbound fraction would have originated from the (usually) male suspect.

Conversely if sperm cells are targeted, then the unbound fraction would have originated from the victim.

Prior art analytical devices and methods generally take about 5-6.5 hours to analyze a cell sample, including initial cell separation, cell lysis and processing of cellular components such as DNA to provide products generated from the cellular components (e.g. STRs). In contrast, the use of the present microdevice shortens the total time to at most about 2 hours.

Exemplary Microfluidic Device and Operation Thereof

The following section describes an exemplary microdevice, and sometimes refers to its use in the processing of a forensic sample such as a sample obtained with a rape kit. However, this section is exemplary; a microdevice may also be used to process other types of biological samples, other types of forensic samples, etc., e.g. as described elsewhere herein.

Procurement and Loading of Sample

Figure 1B:
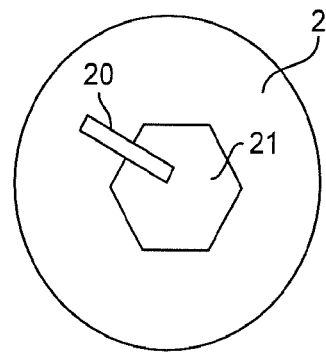

With reference to FIG. 1, in some aspects, a system of the invention includes a microdevice 100 comprising chamber 1 (e.g. a sample-input chamber). Chamber 1 comprises an opening and is configured to receive a sample through the opening, e.g. by receiving a sample collection device, such as a swab, or a portion of a sample collection device, such as a portion of a swab, which contains collected cells. Those of skill in the art are familiar with devices that are used to collect cell samples from a cell source, e.g. swabs with a handle portion and a collection surface (e.g. foam, cotton, etc.) that comes into direct contact with a surface of the cell source. Such samples are generally referred to as "swabs" or "smears".

In some aspects, the cell source is a mammal, such as a human, and the particular source of the cells to be collected is the surface of a tissue, e.g. vaginal tissue, anal tissue, nasal tissue, tissue of the nasopharyngeal cavity, etc. In particular aspects, the human is a (female or male) victim of sexual assault and the cells are collected from the vagina and/or the anus and/or the oral cavity i.e. typical areas of penetration/ejaculation by a perpetrator. However, cells may be taken from any part of the body (e.g. a surface or crevice), that is considered likely to harbor cells suitable for analysis, or from an article of clothing, or from a "wearable" item such as a tampon, a bandage, etc. Those of skill in the art are familiar with the use of collection devices such as swabs to collect cell samples. Examples of suitable collection devices are disclosed, for example, in US patent application pre-grant publications 2013/288863 and 2005/0252820, etc. and are readily commercially available.

In some aspects, prior to analyzing the sample using the microfluidic device described herein, the sample is pre-processed, e.g. to remove unwanted sample components (e.g. debris, tissue fragments, etc.), unwanted cell types (e.g. red blood cells,) or other contaminants, e.g. by centrifugation, filtering, etc. The cells may also be transferred to a biologically compatible liquid carrier and the liquid carrier may be loaded into the device. However, in a preferred time-saving aspect, a cell collection surface or portion of a cell collection surface is loaded directly into the device, e.g. into chamber 1.

In order to conduct a successful analysis, the number of cells of interest in a sample to be processed generally ranges from about 0 to about several millions, and is preferably at least about 10 of each type of cell that is, or is suspected of being, present in a sample, and more preferably at least about 100. For example, for the analysis of sperm, the sample preferably contains at least about 100 sperm cells. However, those of skill in the art will recognize that fewer cells can be detected, e.g. as few as about 10, 20, 30, 40, 50, 60, 70, 80 or 90. By "about" or "approximately", we mean within +/−10% of the indicted value, or less, e.g. within +/−9, 8, 7, 6, 5, 4, 3, 2, or 1% of the indicated value. Once the collection surface of the collection device is placed in chamber 1, cells are eluted, rinsed or otherwise removed from the collection surface and transferred into a predetermined quantity of a suitable biologically compatible medium or buffer. In some aspects, chamber 1 is preloaded with a suitable quantity of medium and the collection surface (or a portion thereof) is placed into the medium. Mixing (agitation) may ensue (e.g. by rocking a support or platform onto which the microdevice is attached or by movement of the collection device). Movement may be induced by a user and/or induced by, e.g., a motor or servomotor. Alternatively, a user of the microdevice may actively flush liquid across the collection surface to dislodge cells into chamber 1. Since the device described herein is a microdevice, the amount of liquid used is generally in the range of from about 10 µl to about 20 µl, (e.g. about 10, 11, 12, 13, 14, 15, 16, 17, 18, 19 or 20 µl, and is typically about 12 to 18 µl, such as about 15 µl.

Suitable biologically (physiologically) compatible media or buffers for containing cells from the biological sample include but are not limited to neutral cell buffers such as water, phosphate buffered-saline, or detergent or enzyme-containing cell lysis buffer.

Chamber 1 (the sample-input chamber) is designed so that liquid comprising cells from the collection surface can egress chamber 1 through an opening or channel which provides fluid communication with chamber 2 (e.g., a differential separating chamber). In some aspects, flow of liquid from chamber 1 to chamber 2 is spontaneous upon and during rinsing of the collection surface, i.e. a channel or opening is present which is of sufficiently large dimensions to allow an aqueous liquid to freely leave chamber 1 but to preclude the collection surface, or portion thereof, to egress when centrifugal force is applied. Alternatively, flow from chamber 1 may be controlled by a valve (e.g. a mechanical, laser, or burst valve, as described elsewhere herein) to restrict backflow into chamber 1 when centrifugal force is applied.

In general, for transfers of materials from one location to another within the microdevice described herein, several different types of micro valves may be used between individual, segregated compartments to control liquid movement including but not limited to: mechanical microvalves, passive capillary valves, "burst" valves, photoresponsive valves (such as laser valves), etc. Examples of microvalves that may be employed include but are not limited to, for example, solenoid microvalves, screw microvalves, pneumatic or "Quake" valves, and laser "tap" valves. In contrast, burst valves take advantage of the surface tension of fluid contained within the device. A combination of channel width and the liquid's surface tension prevents the movement of fluid through a burst valve until sufficient pressure, e.g. from centrifugal force, is applied.

In some aspects, mechanical valves operate through the exploitation of a double sided adhesive and biocompatible film, which permits the valves to remain open after a simple screw is loosened. During centrifugation and PCR, the screw can be tightened allowing the mechanical valves to close.

The burst valves incorporated into this microdevice are generally from about 100-150 µm wide, and remain closed e.g. due to the surface tension of the liquid within the microdevice itself. They open when the the microdevice spins at a high enough speed that the rotational force overcomes the surface tension, permitting the flow of liquid from one chamber to the next.

Selective Capture of Cells of Interest

Chamber 2 is a compartment for receiving (e.g., configured to receive) a liquid sample comprising multiple cell types which may have been transferred from a collection surface, e.g. by prior elution, dispersion, rinsing, etc. as described above. Chamber 2 is an on-chip differential separating chamber which may be configured for differentially separating at least one cell type from other cell types. Chamber 2 comprises a plurality of at least one type of capture molecule 20 specific for binding at least one cell type of interest (i.e., a target cell type) in the biological sample. The capture molecules does not bind, or binds to a lesser extent given the conditions in chamber 2, a remainder of non-targeted cell types different from the cell type of interest. In some aspects, the capture molecule may be a sperm-specific antibody for specifically binding sperm cells. However, this is not always the case. An exemplary microdevice can employ any type of capture molecule that is capable of selectively or specifically binding to and sequestering one or more cell types of interest to the exclusion of other cell types, as described in detail below in the section entitled "Alternative Aspects".

Generally, a capture molecule will exhibit specific binding to the target molecule i.e. the capture molecule does not bind other molecules. "Specific" refers to a capture molecule that binds to only one target molecule (i.e. binds exclusively). In addition, the use of capture molecules that bind selectively is also encompassed. "Selective" implies that formation of a complex with a target molecule is favored over formation of a complex with another target molecule. In general, the capture molecules that are utilized in the present exhibit a binding affinity (Kd) for the target molecule of at least about $10^{-9}$, and preferably about $10^{-12}$. Those of skill in the art will recognize that the binding affinity, and hence the specificity/selectivity of a capture molecule be modified by the surrounding milieu, e.g. the ionic strength, pH, etc. of surrounding media. The binding affinity (dissociation constant) of the capture molecule for non-target cells should be greater than about $10^{-9}$, and preferably is greater than about $10^{-8}$ or more, e.g. greater than about $10^{-7}$, $10^{-6}$ or $10^{-5}$ or even greater. The capture molecule may not exhibit any measureable binding of the non-target species.

Capture molecule 20 is affixed to a solid support or substrate 21, such as a bead, particle, string, etc. A plurality of supports or substrates 21 may be included in chamber 2 (e.g. a plurality of beads may be used). Additionally or alternatively to affixing of capture molecules to a solid support or substrate 21, capture molecules 20 may be attached directly or indirectly to the interior walls of chamber 2, and/or substrate 21 may form part of the interior walls of chamber 2, or be part of the walls. In chamber 2, cells in the liquid sample are combined (e.g. mixed) with capture molecule 20 (capture molecule 20 is contacted by, exposed to, etc. cells in the liquid sample) and capture molecule 20 at least selectively, and preferably specifically, binds to cells for which it is selective/specific. The targeted cells are thereby tethered to substrate 21 via capture molecule 20.

Those of skill in the art are familiar with the immobilization of capture molecules such as antibodies onto substrates such as beads, particles, etc. The capture molecules are generally present (immobilized) on or linked to biologically inert substrates, i.e. substrates that do not bind to sample components, other than through the immobilized antibodies, to the greatest extent possible. Examples of suitable substrate materials include but are not limited to various polymers (e.g. polystyrene, poly(methyl methacrylate, PMMA), magnetic material, superparamagnetic material, various resins (e.g. glass or silica), etc. which are known in the art. The antibodies may be attached (e.g. reversibly or irreversibly) or crosslinked to the beads/particles by any suitable means or methods, so long as the attachment is sufficient to retain the antibodies on the beads/particles throughout the use of the device. Examples of suitable attachment mechanisms include but are not limited to: a biotin-streptavidin linkage, epoxy-based binding, cross-linkage, etc.

In some aspects, capture molecule 20 affixed to substrate 21 is preloaded into the device prior to use of the microdevice (e.g. during manufacture, before a sample is placed in the device). In other aspects, the device contains an optional channel or "vent" (opening) in the surface of the microdevice that leads into chamber 2 through which capture molecule 20 affixed to substrate 21 is loaded into chamber 2 at any suitable time prior to use. For example, capture 20 affixed to substrate 21 may be suspended in a biologically compatible liquid medium and pipetted through the vent and into chamber 2.

In some aspects, the sample that is being tested is a forensic sample, in particular a sexual assault sample that is likely to include sperm. Thus, the cell type of interest that is targeted by the capture molecule may be sperm and the capture molecule may be a sperm selective or sperm specific antibody. The antibodies may not be sperm-specific but rather sperm selective, so long as sufficient selectivity is exhibited to provide a clear separation between sperm and other types of cells likely to be in the sample. Examples of suitable sperm-selective/specific antibodies include but are not limited to: antibodies that selectively bind sperm-head or acrosomal cap proteins such as SP-10, SPAG8, MEA-1, PH-20 (SPAM1), AKAP3, MOSPD3, ADAM2, ZP3, Crisp2, ZP1, ZP2, etc. In addition, antibodies that selectively bind all male cells (e.g.MEA-1) may also be utilized to create true "male" and "female" fractions, thereby eliminating mixtures from sexual assault samples and providing clean single-source profiles. Other options include: ZP3 and ZP2 (both bind to the acrosomal cap), ZP1 (binds to the acrosomal cap; coded by the female and helps bind sperm to eggs), Crisp2 (binds to acrosomal cap and also binds to regulator protein for JNK), SPAG9 (binds to acrosomal cap; associated with infertility); AMS IV-54 (binds to binds to acrosomal cap), SPAG6 (binds to tail, associated with infertility). Alternatively, antibodies that target non-sperm cells of a mixture may be utilized, including but not limited to Cytokeratin 4, Human glandular kallikrien 2, PSA, Prostate mucin antigen SPRR2, CD36, Cytokeratin 10, Collagen XVII, etc.

The sample and the capture molecules (e.g. bead-affixed capture molecules) are mixed for a sufficient time and under conditions suitable to allow most or all of the cells of interest in the sample to bind to the capture molecules. Sufficient "mixing" may be accomplished simply as a result of the flow of sample into the mixing chamber and ensuing molecular collisions e.g. by Brownian motion (pedesis) so that mixing is more or less instantaneous as the sample enters the chamber 2. Alternatively, mixing may be deliberate, e.g. by "rocking" or otherwise moving the device. The time required for mixing/contact between the beads and the sample is generally in the range of from about 20 minutes to about 45 minutes at room temperature, e.g. about 20, 25, 30, 35, 40 or 45 minutes. In some aspects, incubation (and/or other steps of the method) may be done at a temperature that is above RT, e.g. up to about 37° C., so long as the temperature does not damage the microdevice or render the cells or cell products undetectable or otherwise unreactive.

Separation of Cells of Interest

Chamber 2 may comprise one or more valves (e.g. a plurality of valves) by means of which cells bound to a capture molecule are separated from unbound sample components. In some aspects, as depicted in the exemplary illustration in FIG. 1, at least the following selectively sized valves are included: mechanical valve 30 and burst valve 40. Microfluidic device 100 is attachable to centrifugal force (CF) source 200 and in this exemplary embodiment, bound cells of interest are separated from unbound cells as follows: Unbound cells leave chamber 2 by the opening of burst valve 40 upon exertion of sufficient centrifugal force by CF source 200 (e.g. by spinning). The speed and operation of CF source 200 is generally controlled by voltmeter 600 to which it is operably connected. Thus, to leave chamber 2, unbound cells move through open burst valve 40 and into a separate compartment, chamber 3. The burst valve may open directly into chamber 3, or into a channel (e.g. a microchannel) that connects chamber 2 to chamber 3. The amount of CF necessary to cause opening of burst valve 40 is generally in the range of from about 5 to about 15, e.g. about 7 to about 12 relative centrifugal force (rcf) units, for example, about 7, 8, 9, 10, 11 or 12 rcf, such as about 8 rcf.

In some aspects, the source of CF is, for example, a rotatable platform to which the microdevice is attached. For example, the CF source may simply be a modified stir plate modified to rotate. Alternatively, the CF source may be a motor driven spin device manufactured to contain or receive the microdevice. In some aspects, such a device may also provide, for example, a means of attaching one or more other elements such as a heat source (e.g. a Peltier heater), fan, reference cells, etc. Such a purpose-manufactured CF source may give fine tuning control over spin speeds and spin times and may be automated.

Chamber 2 may be configured to retain the capture molecules, substrate, and other matter absent a configuration of valves which permit egress. At least one valve (e.g., microvalve, e.g. burst valve 40) may be configured to prevent egress of the capture molecules affixed to the substrate and any cells bound or sequestered by the capture molecules. Yet, the same valve may be configured to allow egress of at least some components of the biological sample which are unbound or unsequestered by capture molecules. The configuration of the valve (e.g. burst valve 40) may be according to a position of the valve with respect to chamber 2, or barriers (e.g. membranes) within the valve with selective porosity, or size, for example.

Size configuration is an exemplary aspect for controlling egress via burst valve 40. For this aspect, the size (e.g. diameter) of substrate 21 (e.g. beads) on which the bound cells are immobilized is greater than the size of the burst valve opening, so bound cells cannot pass through burst valve 40 but are instead retained in chamber 2. Therefore, the application of CF to the microdevice separates bound and unbound cells. As just described, the burst valve 40 is a passive valve which opens under the influence of a centrifugal force. In some aspects, an alternative valve may be substituted which uses an alternative means of opening. In this case, CF may still be used to promote certain materials within chamber 2 to leave the chamber through the valve when it is open. In some aspects, the width of burst valve 40 when open is in the range of from about 100 to about 125 microns, and is generally at most about 125 microns. Accordingly, the size (which may be a diameter) of substrate 21 is generally in the range of from at least about 200 microns or larger, e.g. from about 190 to about 210 microns. Upon conclusion of application of CF, the burst valve 40 may or may not "close". Cessation of CF renders an actual "closing" unnecessary, once bound cells have been retained in chamber 2 and other cells which did not bind to capture molecules are no longer present (e.g. in meaningful quantity) in chamber 2.

Release of Cellular Components

Following separation of cells of different types using chamber 2 (the differential separating chamber), bound cells retained in chamber 2 and unbound cells in chamber 3 (a lysis chamber) are broken open (lysed) to release cellular components. In some aspects, lysis of the cells in both chambers occurs simultaneously, thereby promoting efficiency. However, aspects of the invention in which cell types are lysed separately, or only one cell type is lysed, etc. are also encompassed. Lysis may be affected by adding a suitable lysis-inducing solution to each of chamber 2 and chamber 3. The solution for each chamber may be the same or different i.e. the same type of solution may be used to lyse both types of cells, or different solutions specific for lysing the specific cell types in each chamber may be used (as an example, sperm cells in chamber 2, epithelial cells in chamber 3). The lysis solutions may be preloaded onto the microdevice into segregated compartments and released from the compartments and into the appropriate chamber at the appropriate time, e.g. upon the application of CF or by means of a mechanical or laser valve. Alternatively, the solutions may be added via an opening or vent in the surface of the device, as described above.

Examples of suitable lysis solutions include but are not limited to: for lysis of most non-sperm cells a standard detergent-containing solution such as a sodium dodecyl sulfate (SDS) lysis buffer may be used, as may lysis solutions comprising enzymes such as protease, elastase, collagenase, trypsin, dispase, mutanolysis, and various recombinant forms thereof. In contrast, to lyse e.g. sperm cells, a standard (e.g. SDS) lysis solution with added dithiothreitol (DTT) may be used; the DTT is needed to break the strong disulfide bonds present in the sperm head. In addition, the solution may contain enzymes such as protease, elastase, collagenase, trypsin, dispase, mutanolysis, and various recombinant forms thereof. Commercial sources of lysis solutions are known, for example, the enzyme solution of the prepGEM® Saliva kit. Those of skill in the art will recognize that lysis solutions can be readily optimized to achieve desired yields of intracellular (subcellular) components.

Heating is generally required for efficient lysis. Thus, the system disclosed herein also includes a heat source, which is generally an infrared (radiant) or Peltier heat source. Such a heat source is described in detail below.

Movement, Storage and/or Processing of Released Cellular Components

Cellular components from the lysed bound sample fraction are transferred from chamber 2 to metering chamber 4 when valve 30 is opened, the geometrical architecture of valve 30 being sufficient to allow passage of cellular components but not substrate 21. Valve 30 may be, e.g., a mechanical, laser, or burst valve. Cellular components from the unbound sample fraction are transferred from chamber 3 to metering chamber 5 upon opening of valve 32, which may be, e.g., a mechanical, laser, or burst valve.

Metering chamber 4 and metering chamber 5 facilitate or mediate the transfer of a portion of the cellular components (e.g. DNA) to storage chamber 6 and storage chamber 7, respectively, without further processing. The stored cellular components represent excess, which can be available for removal and used for other applications, as needed. The volume of material that is designated for storage is generally in the range of from about 5 µl to about 25 µl, e.g. about 10 µl to about 20 µl (such as 10, 11, 12, 13, 14, 15, 16, 17, 18, 19, or 20 µl) and is generally about 12 µl. The transfer takes place by means of a mechanical, laser, or burst valve.

Metering chamber 4 and metering chamber 5 also facilitate or mediate the transfer of a separate (non-stored) portion of the cellular component sample to mixing chamber 8 and mixing chamber 9, respectively, for further processing. The transfer of sample from metering chamber 4 and metering chamber 5 generally occurs via burst valve 41 and burst valve 42, respectively, and is thus initiated by CF. However, the use of mechanical and/or laser valves is not precluded. The level of CF needed to effect the transfer is generally in the range of from about 5 to about 20 rcf, e.g. about 5, 10, 15 or 20 rcf, and is generally about 8 rcf.

Mixing chambers 8 and 9 comprise reagents for further processing of cellular components of interest, e.g. DNA. For example, the reagents may be suitable for conducting PCR or another technique for preparing products generated using e.g. DNA as a template. The reagents may be preloaded into chamber 8 and 9, or may be introduced into chamber 8 and 9 via vents in the surface of the device.

In one exemplary embodiment, the cellular component of interest is DNA and the reaction that is conducted is PCR. For this aspect, examples of PCR reagents include but are not limited to: suitable buffers such as those containing $Mg^{++}$ and needed for elongation; excess nucleotides; enzymes which catalyze elongation; primers specific for amplifying regions of interest within the DNA, e.g. single tandem repeats (STRs), mitochondrial D-loop, or other regions of interest. Alternatively, cellular components such as RNA or miRNAs can be targeted and if so, additional reagents may include but are not limited to reverse transcriptase, fluorophores, etc.

Using DNA and PCR amplification as an example, further mixing of the reagents and the DNA occurs as the mixture travels from mixing chamber 8 and mixing chamber 9 to and through mixing microchannel 10 and mixing microchannel 11, respectively. In some aspects, the mixing microchannels are serpentine (e.g., a curving or tortuous path) to lengthen the distance, and hence the time, of mixing.

For the example of conducting PCR, mixing microchannel 10 and mixing microchannel 11 open into and thus transfer the mixtures contained therein to chamber 12 and chamber 13, respectively. Typically a reaction reference chamber 14 is also provided.

For the example of conducting PCR, chambers 12 and 13 are configured so as to be heated, e.g. by exposure to IR or Peltier (although the use of other heating means is not precluded). Peltier elements generally employ a metal block that is evenly heated and cooled through the use of a solid-state active heat pump that the heats and cools the air. Thus, in some aspects, a system of the invention thus also comprises heat source 300 and cooling fan 400. Heat source 300 and cooling fan 400 may be "non-contact" in that they are positioned to provide heat and cooling without coming into direct contact with the microdevice, i.e. they provide heating/cooling from a distance. Alternatively, they may be "contact" heaters in that they clamp or are otherwise attached directly onto the microdevice. Heat source 300 and cooling fan 400 are operably connected to PC 500, which directly controls the operation of heat source 300 and cooling fan 400, and thus the temperature of the sample. A thermocouple inserted directly into the chip or sitting directly on the Peltier surface sends temperature information to PC 500, which then activates heat source 300 and/or cooling fan 400 as needed. Since inserting a thermocouple directly into the sample could introduce contaminants and particles that could inhibit downstream PCR, thermocouple 15 is instead inserted into separate reaction reference chamber 14 or is placed directly onto the "contact" heating source. In order to insure accurate temperature readings, the reference and sample chambers must be equidistant from the focal point of heat source 300. In preferred embodiments, heat source 300 is an IR lamp, and this direct heating method, combined with low sample volumes, low thermal mass of the chip, and the advantageous interaction of IR radiation with water, allows for the rapid heating and cooling of the sample, reducing the PCR thermocycling time to ~45 minutes e.g. about 30, 35, 40, 45, 50, 55 or 60 minutes.

IR heat sources provide radiation with a peak wavelength ranging from about 780 nm to 1 mm, with short wave or near infrared ranging from 780 nm to 1400 nm, medium infrared ranging between 1400 nm and 3000 nm and far infrared (dark emitters) ranging above 3000 nm. For the present disclosure, the wavelength range that is used is generally from about 1400 to about 3000 nm, and is usually about 2500 nm. Other suitable heat sources include but are not limited to other sources of thermoelectric heating and cooling, such as a Peltier device. In any case, it is generally preferred to have the capability to quickly heat and cool designated chambers of the device in the temperature range of from about 4° C. to about 99° C., e.g. to permit PCR cycling. In some aspects, temperature ramp rates up to about 10° C. per second are used.

Heating for PCR is generally cyclical so as to alternate suitable periods of high temperatures (to denature the DNA and prevent primer binding) with suitable periods of lower temperatures (to allow primer binding and elongation of targeted sequences). Such heating patterns and the determination of heating patterns known in the art and depends, for example, on the sequences of primers and other factors. Heat source 300 is generally capable of simultaneously heating chambers 12 and 13 to temperatures in the range of from about 4° C. for denaturation to about 99° C. for elongation for periods of time ranging from about 5 to 30 seconds for denaturation to about 30 to 60 seconds for elongation. However, in some aspects, the chambers may be heated independently, e.g. the contents of one chamber may undergo PCR with a particular set of requirements and the second chamber may require a different heating pattern, or one chamber may be used for PCR and the other for a different reaction.

Construction of the Microdevice

Capillary action, i.e. the movement of a liquid within the spaces of a porous material due to the forces of adhesion, cohesion, and surface tension, is known in the art for moving liquids through microchannels. A microchannel is generally defined as a fluid passage which has at least one internal cross-sectional dimension that is less than 1 mm and is typically between about 0.1 µm and about 500 µm. Microfluidic devices comprising microchannels such as those which are disclosed herein are generally constructed as multi-layer laminated structures made from a suitable laminate material. Each layer has channels and openings which, when the layers are joined together, form microscale voids and channels for liquid containment and movement. Methods of constructing microscale devices are known, e.g. see U.S. Pat. Nos. 4,989,319; 5,010,951; 5,051,146; 5,204,525; and 6,557,427 and US patent applications 20100279899, 20050007872 and 20040146863, the complete contents of each of which is hereby incorporated by reference in entirety.

Capillary flow within a microdevice may be controlled with or without the application of force, e.g. CF, gravity, etc. The control and pumping of fluids through the channels of the disclosed microdevice is accomplished, for example, by pressure exerted by CF. However, variations of this mechanism may also be used. For example, in some aspects, capillaries may be of a smaller cross section or diameter in a direction transverse to the direction of flow and the cross section or length in the direction of flow may be similar or may differ by a factor of ten or more, depending on the function of the capillary and chambers to which it connects, thereby causing a net, directed flow in one direction. In addition, conical capillaries or different surface treatments at different points in a capillary may be employed to achieve differing surface tensions at the ends of a capillary, thereby causing a fluid plug to move through the capillary toward the location of lower pressure. Any mechanism of ensuring the flow of liquid in a desired direction and at a desired time may be used in the construction of the disclosed microdevices.

The compositions of channels and chamber walls is selected so as to provide a desired degree of wetting and surface tension. For example, the device may be made of glass, plastic (e.g. poly(methyl)methacrylate or "PMMA", polyester, etc.), quartz, ceramic, or various silicates, etc., or some combination of these and/or other materials.

Typically, the general layout of the microdevice is first planned, e.g. to include the requisite number of chamber, channels, vents and other openings, etc. and is drawn with a drawing or design software program which is then interfaced with an ablation system that can cut or etch suitable patterns of channels, voids, etc. into a plurality of layers of suitable composite. For example, the required designs are ablated into or onto at least a top, bottom and middle layer having dimensions ranging from about 0.1 to about 2 mm 0.5 mm, and the layers are then bonded e.g. using thermal or other suitable bonding (e.g. adhesive, etc.).

Uses of the Microdevice

The microdevices described herein can be used for a wide variety purposes in many scenarios. For example, they find application in forensics in cases in which it is necessary to analyze samples which include, or are likely to include, more than one type of cell. The ability to rapidly conduct both separation and processing of cells and cellular materials using a single inexpensive device is highly advantageous. The devices also offer a high degree of flexibility in that the capture molecules that are included in the device may be specific for any cell type of interest, and the subsequent processing steps may be any which ultimately provide a useful product of interest.

For example, STR amplicons can be rapidly and inexpensively produced from a sample comprising sperm. The amplicons that are produced by the microdevice constitute a "DNA profile" of the individual from whom the sperm originated, and the profile can be compared to STR profile databases to identify the perpetrator, thereby facilitating prosecution and conviction, or alternatively, exonerating suspects who are not guilty. In some aspects, what is amplified is 15 human short tandem repeat (STR) loci and Amelogenin, or other markers used for human identification and gender determination.

Alternative Aspects

The generic microdevice depicted in FIG. 1 comprises a single "chamber 1" for receiving a sample to be analyzed, a single "chamber 2" for differential separation, etc. However, the disclosure also encompasses microdevices with a plurality of such chambers so that multiple samples, or duplicates of one sample, can be analyzed in a single device. For example, the microdevice can be resized for scalability in order to process multiple samples at the same time. Thus, in some embodiments, a single chip may comprise a plurality of flowpaths, or a plurality of independent or semi-independent circuits. In the case of semi-independence, it may be that a chip keeps the cells of one sample isolated at all times from the cells of any other sample, but commons sources of solutions (e.g. wash solutions, elutions, lyse solutions, etc.) are provided for a plurality of otherwise independent circuits. Further, additional steps such as washing steps (e.g. to change buffers or buffer conditions, to remove unwanted material from a sample or reaction intermediate, etc.) may be added as needed, as may chambers, conduits, etc. for containing and/or transferring a liquid that is used as a wash. Likewise, multiple selection steps may also be included, e.g. a first selection of a particular cell type of interest and a second selection step to select particular variants of that cell type.

Further, alternative types of chambers such as pinwheel chambers may also be incorporated. Such chambers make use of superparamagnetic beads that form pinwheel-shaped aggregates when DNA is present.

In addition, what is shown in some of the figures and described with respect to some exemplary illustrative embodiments is the processing of two cell types from a sample, only one of which is "captured" and retained to facilitate separation. However, the disclosure is not limited to such aspects: multiple chambers and channels may be included in the microdevice so that portions or aliquots of a sample are exposed to several different capture molecules or capture "mechanisms", i.e. the sequestration of a particular cell type need not be based on selection by a biological molecule. Any capture mechanism may be used, so long as a sufficient portion of the cells of interest are captured and thus separable from other sample components. In addition, the entities that are "separated" in the early steps of device use need not be whole cells; rather, any entity that is subject to "capture" (e.g. irreversible or high affinity binding) to a capture agent may be sequestered as described herein and then separated from other components of a sample. Thus, samples comprising multiple (at least two, three or more, etc.) types of cells that are separable, or samples comprising multiple (at least two, three or more, etc.) types of molecules (e.g. macromolecules) that are separable, may be analyzed using the methods.

Examples of other types of cells that may be present in a sample and that may be separated and processed using a microdevice as described herein include but are not limited to mucosal epithelial cells from different individuals (e.g. vaginal or buccal cells), mucosal epithelial cells from non-mucosal epithelial cells (e.g. skin cells), or male cells from female cells (regardless of type).

Examples of molecules or macromolecules that may be present in a sample and that may be separated and processed using a microdevice as described herein include but are not limited to RNA, miRNA, drug analytes, etc.

In some aspects, the capture mechanism that is utilized in the device is that of a "capture molecule". However, non-molecular based capture may also be employed. For example, some materials have a high affinity for e.g. nucleic acids or other biological molecules and may be used.

In some aspects, the capture mechanism does involve molecules which bind to and form a complex with a cell or molecule of interest, and the molecules may be antibodies. However, other strategies for sequestering a cell or molecule of interest may also be used. For example, various receptor-ligand binding pairs may be adapted for such uses, e.g. various agonists or antagonists, etc. Any binding reaction that allows selection of a cell type or molecue of interest as described herein may be utilized.

Exemplary reactions that have been described as taking place within the subject microdevice include cell lysis and PCR amplification of DNA. However, these are not the only reactions that cells/molecules that are processed as described herein can undergo. For example, any process involving temperature controlled incubations or centrifugal motion may also be pursued with this microdevice.

Methods

The disclosure also provides methods of separating entities in a sample from each other and subsequently processing one or more of the entities, i.e. causing the entities to undergo a reaction e.g. whereby products generated from the entities are formed. Typically, the sample is a biological sample and the "entities" are biological in nature, e.g. cells, macromolecules, etc. The method involve providing or procuring a sample of interest, loading the sample into a microdevice as described herein and, within the microdevice, separating one or more components of interest in the sample from other components in the sample. Thereafter, the separated components are transferred to separate locations within the device to undergo one or more processing reactions. In the case of cells, such reactions may include cell lysis to release cell components, and further processing of one or more of the components e.g. to permit determination and/or confirmation of one or more identifying characteristics of the sample, such as the types of cells in the sample, and/or the origin of the cells.

In an exemplary aspect, what is provided is a method to establish the identity of a perpetrator of sexual assault. In this aspect, typically a suitable biological sample is obtained from the putative victim (e.g. a sample that is likely to contain cells from the criminal, such as sperm cells), and the sample is subject to analysis using the microdevice described herein. The sample is introduced into the microdevice and within the microdevice, sperm cells are separated from other sample components (e.g. from epithelial cells), are lysed to release DNA, and the DNA undergoes PCR in order to produce a product (e.g. amplicons from STRs) that are specific to individuals. All reactions, including steps of separation, lysis and PCR amplification, advantageously take place rapidly "on-chip". Amplicons are then provided for further analysis, e.g. by comparison of the pattern to a database with the hope of matching the pattern with that of an individual whose data is already present in the database.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method may be carried out in the order of events recited or in any other order which is logically possible.

EXAMPLES

Example 1. A Rotational Platform-Driven Microdevice for Differential Separation, Purification, and Amplification of Sexual Assault Forensic Samples Introduction The field of microfluidics employs devices capable of reducing the amount of time, reagents, and space required to perform scientific processes. Microfluidic devices, or microdevices, were first developed for forensic use in the early 1990's. Prior to this time, these were primarily used in fields outside of biology since DNA testing required higher volumes than would be easily acceptable by any microdevice. Initially, biological microdevices focused on DNA separation, but as time progressed, additional steps of typical DNA workflow were modularized and integrated onto those devices. As additional modules were incorporated onto microdevices, the microfluidics associated with these devices became increasingly complex. Originally, simple gravitational microdevices were used for fluid movement from one module to the next, but this quickly gave way to those controlled with pneumatic pressure and actuators. With this, the idea of micro total analysis systems (μTAS) was developed. This is often described as a "lab-on-a-chip" to those outside of the scientific community. When first developed, microdevices were made of glass, but as technologies became more sensitive, the risk of contamination increased. Thus, the field moved from reusable glass microdevices (cleaned between uses) to disposable microdevices, typically made of plastic.

Microdevices have many advantages over traditional, manual DNA analysis methods. First, startup costs to a lab are significantly reduced, as microdevices use less expensive material and are often used in conjunction with less expensive instrumentation (2). Second, microdevices further reduce cost by using smaller volumes of each reagent needed to extract and amplify DNA. Third, microdevices are ideally closed systems, meaning there are no tube transfers that occur in the workflow. This all but eliminates the risk of contamination from sample-to-sample or examiner-to-sample. Lastly, samples are capable of being processed significantly faster using microdevice technologies. Currently processing a forensic DNA sample can take as long as eight hours, not including data analysis time. Microdevices, such as the one described herein, can reduce this time by three to four hours. This improvement not only contributes to a reduction in the backlog of samples to be processed, but also frees up analysts' time to focus on data interpretation, which tends to be the most complex and time-consuming part of the entire analytical process.

Currently, commercially available microdevice-driven instruments developed for the forensic community are focused on the rapid analysis of reference samples. These microdevices have been developed for use with tabletop instruments, which are capable of producing an STR profile from a reference swab in ~2 hours. These instruments, and the development of the machinery needed to produce these devices, are commonly referred to as "rapid technology".

Sexual Assault Sample Processing

Cox et al. (Cox, et al. ELECTROPHORESIS. 2016; 37(23-24):3046-3058) were able to develop a microdevice capable of processing samples comprising a single known type of cell through the amplification stage in the DNA workflow. While known reference samples (typically received as buccal swabs) comprise a large percentage of the samples a forensic lab processes, forensic evidence samples, which are often compromised and contain DNA from multiple contributors, comprise the remainder. Sexual assault cases are very common in forensic DNA labs and can contribute up to 52% of the samples a lab processes; each year the number of these cases that are backlogged grows. As the media draws more attention to these backlogged sexual assault cases, it has become imperative that those samples are prioritized in forensic labs. Unfortunately, sexual assault samples take significantly longer to process than other forensic samples due to the manual, tedious bench procedures as well as lengthy, complex mixture interpretation that is often inevitable, as these samples most frequently consist of DNA from multiple contributors. In order to obtain a DNA profile from a sexual assault sample it must go through a specialized DNA lysis and purification process, commonly referred to as a "differential extraction". This process is used to separate sperm cells (likely from the male contributor/suspect) from epithelial or non-sperm cells (primarily from the victim). Differential extraction procedures typically include an initial lysis of the non-sperm cells using sodium dodecyl sulfate (SDS). The sample is then spun at a high speed (~10,000×g), causing the intact sperm cells to pellet. The now lysed non-sperm fraction (in the supernatant) can then be transferred into another tube. Next, dithiothreitol (DTT) and standard lysis solution can be added to the tube containing the sperm pellet. The DTT is needed to break the strong disulfide bonds present in the sperm head.

Once separated and lysed, the sperm and the non-sperm cells move along the DNA purification process as two separate samples.

The primary objective of this research was the development of a novel on-chip module for separation of sperm and non-sperm cells with the goal of easy integration onto a forensic poly(methyl methacrylate)(PMMA) microdevice. The microdevice utilizes centrifugal force and a series of valves for microfluidic control. The centrifugal force is exerted by a modified stir plate that is attached to a voltmeter for fine control of the rotational speed. There are two different types of valves in this system: mechanical valves and passive capillary, or "burst," valves. The mechanical valves are open until pressure is applied to physically close the valve. Alternatively, the burst valve (~100 μm wide) takes advantage of the surface tension of the fluid contained within the device. The combination of the channel width and the liquid's surface tension prevents the movement of fluid until enough external pressure, in this case from centrifugal force, is applied. Amplification of STR loci is performed on the initial swab device using Infrared mediated-PCR (IR-PCR).

IR-PCR uses a PC-controlled infrared heat lamp and fan to directly control the temperature of the sample. A thermocouple inserted directly into the chip sends temperature information to the PC, which then activates the lamp or fan as needed. Since inserting the thermocouple directly into the sample could introduce contaminants and particles that could inhibit downstream PCR, it is instead inserted into a separate reference chamber. In order to insure accurate temperature readings, the reference and sample chambers must be equidistant from the focal point of the IR lamp. This direct heating method, combined with low sample volumes, low thermal mass of the chip, and the advantageous interaction of IR radiation with water, allows for the rapid heating and cooling of the sample, reducing the thermocycling time to ~45 minutes.

Antibody Mediated Sperm Cell Capture

The focus of this work was the development and integration of a sexual assault module into a microdevice. In the sexual assault microchip described herein, sperm cells are separated from non-sperm cells of sexual assault samples using an antibody-mediated sperm cell capture mechanism. As the nuclear DNA of sperm cells is held in the head of the sperm and sperm heads are often and easily detached from sperm tails during laboratory processing, antibodies that selectively bind sperm-head or acrosomal cap proteins (such as SP-10, SPAG8, etc.) were selected for testing. In addition, a third antibody that selectively binds all male cells (MEA-1) was tested, which if successful would create a true "male fraction" and "female fraction". This approach could eliminate mixtures entirely from sexual assault samples, providing clean single-source profiles for these samples. Once an appropriate antibody or combination of antibodies had been chosen, they were be used to coat small polystyrene beads (microspheres) that were used in the capture assay. Antibodies were permanently bound to the beads using a biotin-streptavidin linkage.

There were several additional considerations that had to be weighed in order for this approach to be effective and successful. First, the antibody must selectively bind to sperm cells and not non-sperm cells, namely the epithelial cells that constitute the bulk of the non-sperm cellular content of sexual assault samples. Further, the antibody binding must be efficient and able to capture a high percentage of the (potentially low-level) sperm cells present in the cellular mixture. Second, the bead chosen for the capture assay needed to be composed of a material that does not bind DNA in order to avoid saturation of the bead by cell-free DNA that may be present in the sample or by DNA liberated by cell lysis. This eliminates the potential use of standard silica beads. Last, the beads selected for antibody capture must be large enough to prevent passage through a burst valve. This will be dictated by the channel sizes, which are based on microdevice design and the capabilities of e.g. laser cutters used to fabricate the microchips.

Methods and Materials

Sample Collection & Preparation

Three male volunteers provided semen samples and three female volunteers donated vaginal swabs; all volunteers also submitted two buccal swabs for use as reference DNA samples. The semen samples were divided into 100 μL aliquots and stored at −20° C. Semen swabs were generated by dipping foam swabs in ~100 μL neat semen. Mock post-coital swabs were prepared by dipping dried vaginal swabs in ~100 μL of neat semen. All swabs were dried and then stored at 4° C. All samples used in this study were collected in accordance with VCU approved IRB protocol HMW20002942.

Sexual Assault Microchip Architecture

The design for the sexual assault microdevice was drawn in AutoCAD LT® 2004 software (Autodesk® Inc., San Rafael, CA). The schematics were then exported to VLS 3.5 software to interface with the VersaLaser® 3.50 $CO_2$ laser ablation system (Universal Laser Systems, Scottsdale, AZ), which was used to cut the designs from 0.5 mm (top and bottom layers) and 1.0 mm (middle layer) sheets of PMMA (Astra Products, Inc., Baldwin, NY). Layers were bonded using thermal bonding.

Evaluation of Custom prepGEM® Differential Method

A custom-modified differential lysis protocol was developed for use with semen/sperm-containing samples using the prepGEM® Saliva kit (ZyGEM™, Hamilton, New Zealand). The performance of this method was evaluated by comparing resulting DNA yields to those obtained using a more traditional differential lysis/DNA extraction method. All semen samples used in this study were diluted 1:2 in PBS solution. For the custom method using ZyGEM™ prepGEM® Saliva for lysis of sperm cells, 10 μL of each diluted semen sample was added to 1 μL of the prepGEM® enzyme, 10 μL of 10× Blue Buffer (ZyGEM™) and 79 μL of water. Samples were heated for 3 minutes at 75° C. in a Perkin Elmer GeneAmp 9600 (Perkin Elmer, Waltham, MA) before being spun for 5 minutes at 10,000×g. The supernatant was removed and placed into a clean tube labeled non-sperm fraction (NSF). The remaining sperm pellet was then re-suspended in a solution containing 1 μL of the prepGEM® enzyme, 10 μL of 10× blue buffer, 4.5 μL of 1M DTT, and 74.5 μL of water. The tube was heated as described above for 3 minutes at 75° C. and was labeled as the sperm fraction (SF).

For samples processed using a traditional differential lysis and DNA extraction approach, 10 μL of each diluted semen sample was lysed by adding 400 μL of Stain Extraction Buffer (10 mM Tris, 100 mM NaCl, 10 mM EDTA, 2% SDS, pH 8.0) and 15 μL of 20 mg/mL proteinase K) followed by a two hour incubation at 56° C. Following incubation, the samples were spun at 10,000×g for five minutes. The supernatant was removed and placed into a new tube labeled non-sperm fraction (NSF). Next, each sample pellet was re-suspended in 200 μL of PBS, 20 μL of Qiagen™ Protease, 20 μL of 1M DTT, 200 μL of Qiagen™ Buffer AL, and incubated for one hour at 56° C. DNA purifications were performed on both fractions (NSF and SF) using the QIAamp® DNA Blood Mini Kit (Qiagen™, Hilden, Germany) according to manufacturer's protocol with a final elution volume of 75 μL.

DNA Quantcation

All DNA samples used in this study were quantified using Investigator® Quantiplex HYres kit (Qiagen™) on an ABI 7500 Fast Real-Time PCR system (Life Technologies™, Foster City, CA) using the manufacturer's protocol modified for half-volume reactions (17).

Antibody Evaluation Via Flow Cytometry

After an extensive review of available sperm-specific antibodies, three antibodies were selected for testing: sperm protein 10 (SP-10), sperm associated antigen 8 (SPAG-8), and male enhanced antigen 1 (MEA-1). For an preliminary evaluation of antibody-binding efficiency, samples were analyzed by flow cytometry using either fluorescently tagged MEA-1 antibodies (allophycocyanin or APC), SP-10 antibodies, or SPAG-8 antibodies (both labeled with Alexa Fluor 647) (Bioss, Woburn, MA). To prepare semen samples for flow cytometry, previously described methods were tested unsuccessfully (19), thus a modified cell preparation protocol was developed. For each sample tested (n=3), 100 µL of neat semen was spun at 800×g for 5 minutes. Following this spin, the supernatant was removed, the cell pellet was resuspended in 300 µL of cell staining buffer (SouthernBiotech, Birmingham, AL), and the sample spun again at 800×g for 5 minutes. This wash step with cell staining buffer was repeated one additional time. The resulting cell pellet was resuspended in 25 µL of rabbit IgG (0.16 mg/mL) (Bioss) and incubated at room temperature for 10 minutes. Next, 25 µL of SP-10, SPAG-8, or MEA-1 antibody solution (20 ng/µL) was added to each sample. The samples were then wrapped in foil and incubated at 4° C. for 35 minutes. Following this incubation, samples were then spun at 800×g for 5 minutes, the supernatant removed, and the pellet re-suspended in 300 µL of cell staining buffer. This wash step was repeated twice more. Lastly, the samples were then spun at 800×g for 5 minutes, the supernatant removed and the samples resuspended in 200 µL of cell staining buffer. All prepared cell solutions were then run on a FACsCalibur flow cytometer (BD Biosciences, San Jose, CA) with the forward scatter set to E-1 and a threshold of 273 fluorescence units (FLU), the side scatter set to 273 FLU, and FL-4 set to 601 FLU. In order to isolate and evaluate sperm cell populations a gate was established based on cell size and density as inferred from the forward scatter and side scatter. The run was stopped when either 1,000,000 cells were detected in the gated population or 30 seconds had elapsed, whichever happened first. These samples were then compared to an unstained isotype control in order to determine the percentage of the cells that were positively stained.

Antibody-Bead Complex Testing Off-Chip

Next, the proposed bead-mediated antibody binding efficiency was tested. Streptavidin-labeled polystyrene beads ~200 microns in size and 1% w/v (Spherotech, Lake Forest, IL) were selected for use in this study. In order to bind the tested antibodies to the beads, 94 of bead solution (approximately 20 beads) per sample to be processed was added to a total of 1 mL of PBS followed by a spin at100×g for 60 s. The supernatant was discarded and the wash step was repeated twice more. After the final spin, the supernatant was discarded and ~0.167 µg of the biotin-labeled antibody was added for each sample to be processed. The bead: antibody mixture was incubated at room temperature for 30 minutes with gentle agitation. Following incubation, five additional washes were performed with 1 mL PBS as described above. After the final spin, the bead pellet (containing the antibody-coated beads) was re-suspended in 9 µL of PBS per sample to be processed.

In order to bind target cells to the antibody-coated beads, 9 µL of the antibody-coated bead solution was added to 10 µL of a 1:2 semen dilution for each sample tested (n=3). The samples were incubated for 35 minutes at room temperature to bind the sperm cells to the antibody-coated beads. The samples were then spun at 100×g for 60 s.

The supernatant was removed into a new tube for DNA preparation. For DNA preparation of bound cells, the bead pellet was resuspended in 1 µL of the prepGEM® enzyme, 10 µL of 10× Blue Buffer (ZyGEM™), 4.5 µL of 1M DTT and water to 100 µL total volume. The supernatant fraction prepped by adding 1 µL of the prepGEM® enzyme, 10 µL at of 10× Blue Buffer (ZyGEM™), and water to 100 µL total volume. Both fractions (supernatant and bead pellet) were then heated at 75° C. for three minutes prior to DNA quantification as described above. To provide a basis for comparison, two additional sample groups were processed—samples incubated with no antibody-coated beads (No beads) and samples incubated with non-coated beads (Naked beads). All samples were tested in duplicate.

Antibody-Bead Complex Testing On-Chip

In order to ensure that the antibody-bead complex would bind sperm within the plastic environment of the proposed microdevice, bead-mediated antibody binding was tested on a simple microdevice whose design consisted solely of an inlet reservoir (antibody binding chamber), a mechanical valve, and an outlet reservoir (FIG. 1). This simple chip was prepared as a quick and easy way to determine if binding would occur in the plastic microdevice environment (on-chip) as it occurs in the tube-based assay (off-chip). Antibody-coated beads for on-chip testing were prepared prior to testing, as described above. To test on-chip binding, 10 µL of a 1:2 semen dilution for each sample tested (n=3) was added to the inlet reservoir along with 9 µL of antibody-coated beads. The sample was mixed by briefly manually pipetting and was then incubated in the microdevice for 35 minutes at room temperature to allow the sperm cells to bind. Finally, in order to test the movement of the samples through the chip architecture, the mechanical valve was opened and the microdevice was spun for 2 minutes at 800 rpm on a custom built rotational device made from a modified stir plate, as described by Cox et al. (2). Sample were manually pipetted from the outlet reservoir and stored in 1.5 mL microcentrifuge tubes for further processing. For controls, 10 µL of each semen dilution was processed a second time on another simple microdevice but without the antibody-coated beads (No beads). After removal from the microdevice, samples were spun in a microcentrifuge for 1 minute at 800×g to pellet the beads. The supernatant was removed to a new tube. Both the supernatant and bead pellet were further processed using the custom modified ZyGEM™ prepGEM® Saliva differential lysis and DNA liberation method described above followed by DNA quantification using the Investigator® Quantiplex HYres kit (Qiagen) method, as described above.

Sexual Assault Microdevice Testing

Figure 2A:
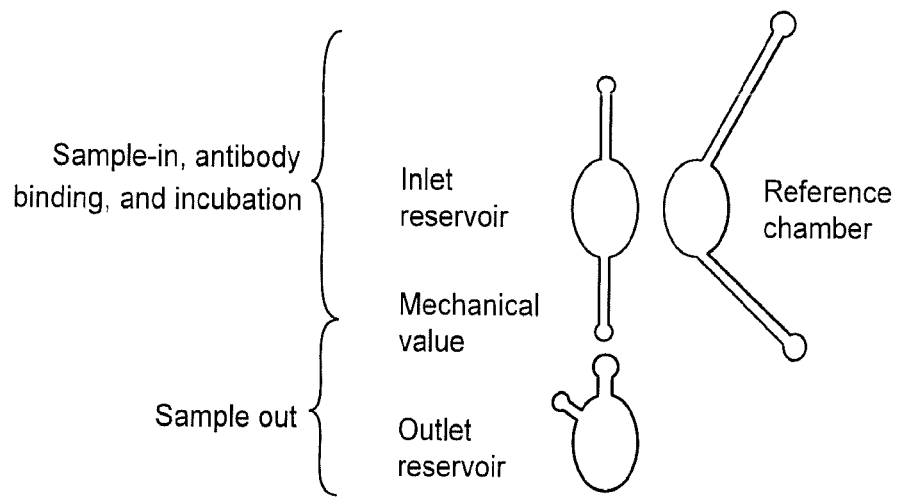
FIGS. 2A and B. A, Simple microdevice module design for on-chip antibody-bead binding efficiency testing. A simple microdevice was designed to test the sperm binding efficiency of the antibody-coated polystyrene beads on-chip. This device contained a single module that included an inlet reservoir and an outlet reservoir separated by a mechanical valve to allow for the testing of the antibody-bead binding and its ability to subsequently move successfully through a microdevice made of materials identical to those proposed for use with the exemplary new sexual assault microdevice. B, Schematic of sexual assault microdevice. All features involved in the reaction and metering schemes are identified. Cell separation will occur in the antibody binding chamber using antibody-labeled beads to facilitate direct binding to sperm cells, forming complexes that are too large to fit through the burst valve (**) when spun on the rotational platform. After a simultaneous lysis of the unbound fraction and DTT-facilitated lysis of the bound sperm cells, a mechanical valve is opened (*1) to allow liberated DNA from the bound fraction to move into the holding chamber. This architecture thus allows for an antibody-mediated separation of sperm cells and non-sperm cells into separate, but identical, side-by-side chambers. Following separation bound and unbound fractions, a second pair of valves can be opened (*2) and the microdevice spun to allow for movement of the liberated DNA samples into side-by-side PCR metering chambers. These chambers allow for side-by-side processing of both the bound (sperm) and unbound (non-sperm) fractions.
Figure 2B:
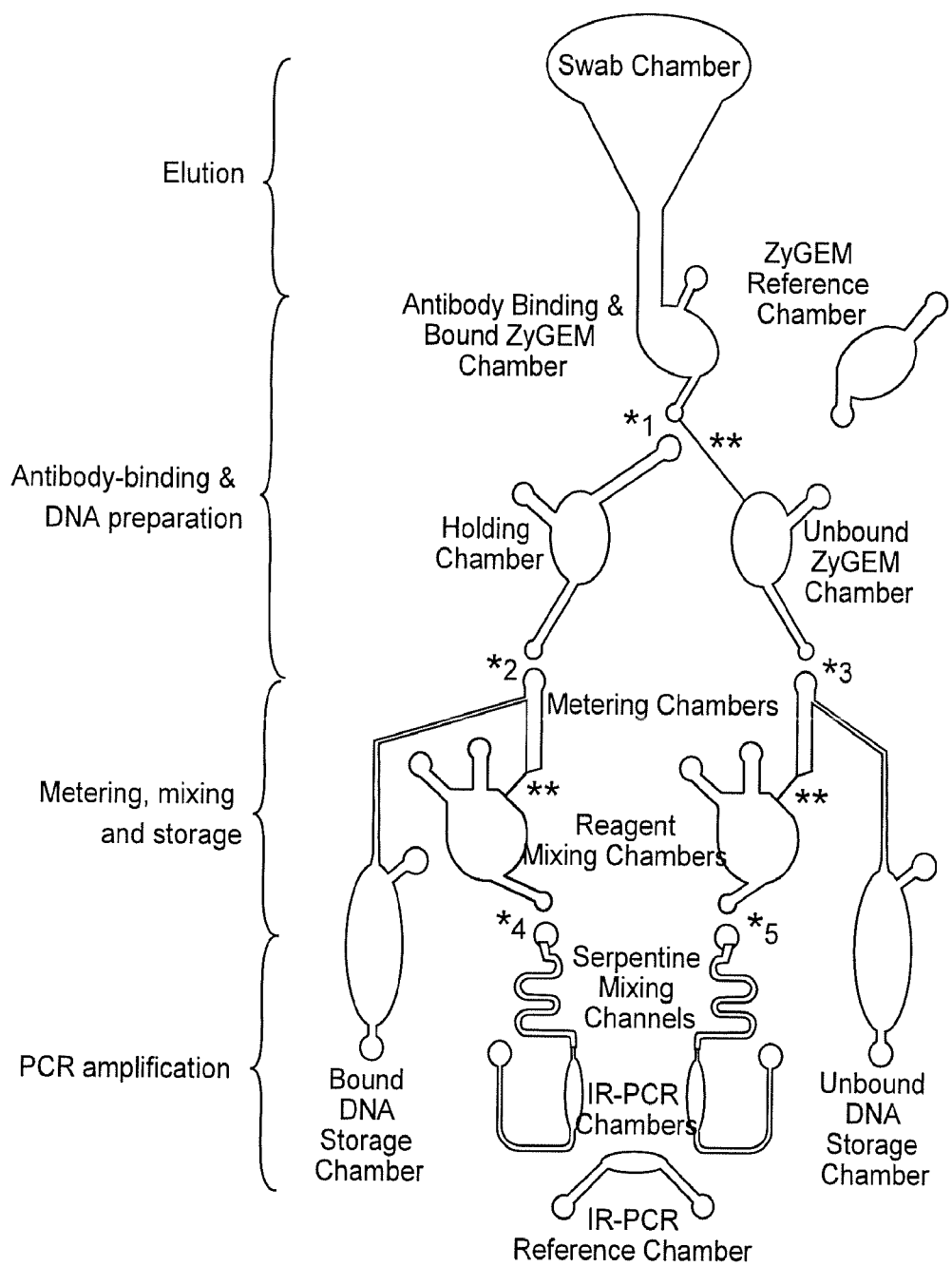

After successful bead-mediated antibody binding results were observed using the simple chip design, the bead capture and liquid separation mechanisms were tested using the proposed integrated sexual assault microdevice (FIG. 2). Antibody-coated beads for testing on the sexual assault microdevice were prepared prior to testing, as described above, except the antibody-coated beads were ultimately resuspended in an 8 µL mix containing 0.8 µL 10× Blue buffer (ZyGEM™), 0.32 µL prepGEM® enzyme (ZyGEM™), and 6.88 µL water.

For microdevice runs, one sixth of a dry semen, vaginal, or mock postcoital swab (n=3 for each) was placed in the swab chamber with 1.8 µL 10× Blue buffer, 0.72 µL prepGEM® enzyme, and 15.48 µL water, and the swab was agitated with a pipet tip to loosen cells. The swab cutting was then removed and 8 µL antibody-coated bead mixture (described above) was added. The swab chamber was sealed with PCR film to prevent evaporation, and the sample was incubated in the microdevice at room temperature for 35 min. Following incubation, all mechanical valves were closed, and the microdevice was spun 2 min at 500 rpm using the custom built rotational device (described above) to move the unbound cells through the burst valve into the unbound ZyGEM™ chamber. Next, a mix containing 1.4 µL 10× Blue buffer, 0.56 µL prepGEM® enzyme, 0.63 µL 1M DTT, and 11.41 µL water was added to the bound ZyGEM™ chamber. The ZyGEM™ reference chamber was filled with water and a type T thermocouple (Physitemp Instuments, Clifton, NJ) was inserted, all ports on the chip were sealed with PCR film, all mechanical valves were closed, and the chip was heated for 3 min. at 75° C. on a custom-built IR-PCR device (2,11,13). After heating, mechanical valve #1 was opened, and the liquid in the bound ZyGEM™ chamber was spun through into the holding chamber for 2 min at 800 rpm. Both bound and unbound fractions were then manually removed from the microdevice for downstream processing. DNA quantification was achieved for all tested samples using the Investigator® Quantiplex HYres kit (Qiagen) method, as described above.

For comparison, another one sixth of each postcoital swab tested on the sexual assault microdevice (n=3 for each) was processed using each of the standard tube-based differential lysis and DNA purification methods described above (custom modified PrepGEM® method and QIAamp® method). Finally, one sixth of each postcoital swab was processed without a differential lysis procedure at all with DNA extraction using the QIAamp® DNA Blood Mini Kit (Qiagen™, Hilden, Germany) according to manufacturer's protocol with a final elution volume of 75 µL.

DNA quantification was achieved for all tested samples using the Investigator® Quantiplex HYres kit (Qiagen) method, as described above.

STR Amplification

Multiplex STR amplification of all DNA samples was achieved using a GeneAmp® 9600 PCR System and a modified version of the manufacturer's recommended protocol for the AmpFCSTR™ Identifiler™ STR kit (ThermoFisher Scientific, Waltham, MA). Thermocycling conditions included a pre-denature step at 94° C. for 11 min, followed by 28 cycles of: denature 94° C. for 1 min, anneal 59° C. for 1 min, extension 72° C. for 1 min, and final post-extension step of 60° C. for 90 min. Amplification reactions consisted of 5.7 µl of AmpFCSTR™ PCR reaction mix, 2.0 µl of AmpFCSTR™ Identifiler™ primer set, 0.20 µl of AmpliTaq Gold® DNA polymerase (ThermoFisher Scientific), 2.1 µl of TE buffer, and 5 µl of 0.2 ng/µl template DNA.

DNA Fragment Size Separation & Analysis

All STR-amplified samples were separated by capillary electrophoresis (CE) on an Applied Biosystems® 3130 Genetic Analyzer (ThermoFisher Scientific) using Data Collection software version 3.1 (ThermoFisher Scientific). For this step, 1.2 µl of amplified sample was added to 12.0 µl formamide (ThermoFisher Scientific), and 0.1 µl GeneScan™ 500 LIZ™ size standard (ThermoFisher Scientific). CE run conditions followed the manufacturer's recommendations and included use of POP-4® polymer (ThermoFisher Scientific), a 36 cm capillary array (ThermoFisher Scientific), and a 10 sec 3 kV injection. Electropherograms generated were analyzed using GeneMapper® v4.1 software (ThermoFisher Scientific). An analytical peak height threshold of 50 rfu was used.

Data Analysis

For all studies described in this work (except for the flow cytometry studies), tested sample groups were compared by using DNA quantifications expressed as either total DNA yields (ng) or as a percent of total DNA yield along with standard deviations. Results of experimental groups were compared using a Student's T test or a two-way ANOVA to determine significance (a=0.05). Tukey HSD post-hoc tests were performed where appropriate to determine which groups were most contributing to the differences noted.

Results & Discussion

Sexual Assault Microchip Architecture

The schematic showing the architecture for an exemplary sexual assault microdevice as shown in FIG. 2. This design takes advantage of the small width of the burst valve channel to separate the sperm and non-sperm cells. With the sperm cells bound to the ~200-micron antibody-coated beads, they are no longer be able to pass through the burst valve (~100 microns) when the microdevice is spun using the rotational platform. Thus, the first spin, (designed to open the burst valve) allows only unbound (non-sperm cells) to move down the right side of the microdevice to the unbound ZyGEM™ DNA preparation chamber, leaving the sperm-bound bead complex in the antibody binding chamber. Next, a ZyGEM™ mix containing DTT is added to the bound ZyGEM™ chamber and the entire microdevice is moved to the IR-PCR device for simultaneous DNA liberation. After heating, the first mechanical valve is opened, allowing the liberated DNA from the bound ZyGEM™ chamber to be spun through to the holding chamber. All architecture downstream of the DNA preparation chambers allows for side-by-side processing of the bound (sperm) and unbound (non-sperm) fractions. IR-mediated STR amplification is optimized and used, allowing for amplicon removal and off-chip CE processing using standard default settings and routine sample preparation protocols. Thus, after separation of sperm and non-sperm cells in the upstream modules and a brief ~45 minute amplification step, the PCR products can be are easily separated from the sexual assault microdevice for traditional CE-based fragment separation and detection.

Evaluation of Custom prepGEM® Differential Method

Figure 3:
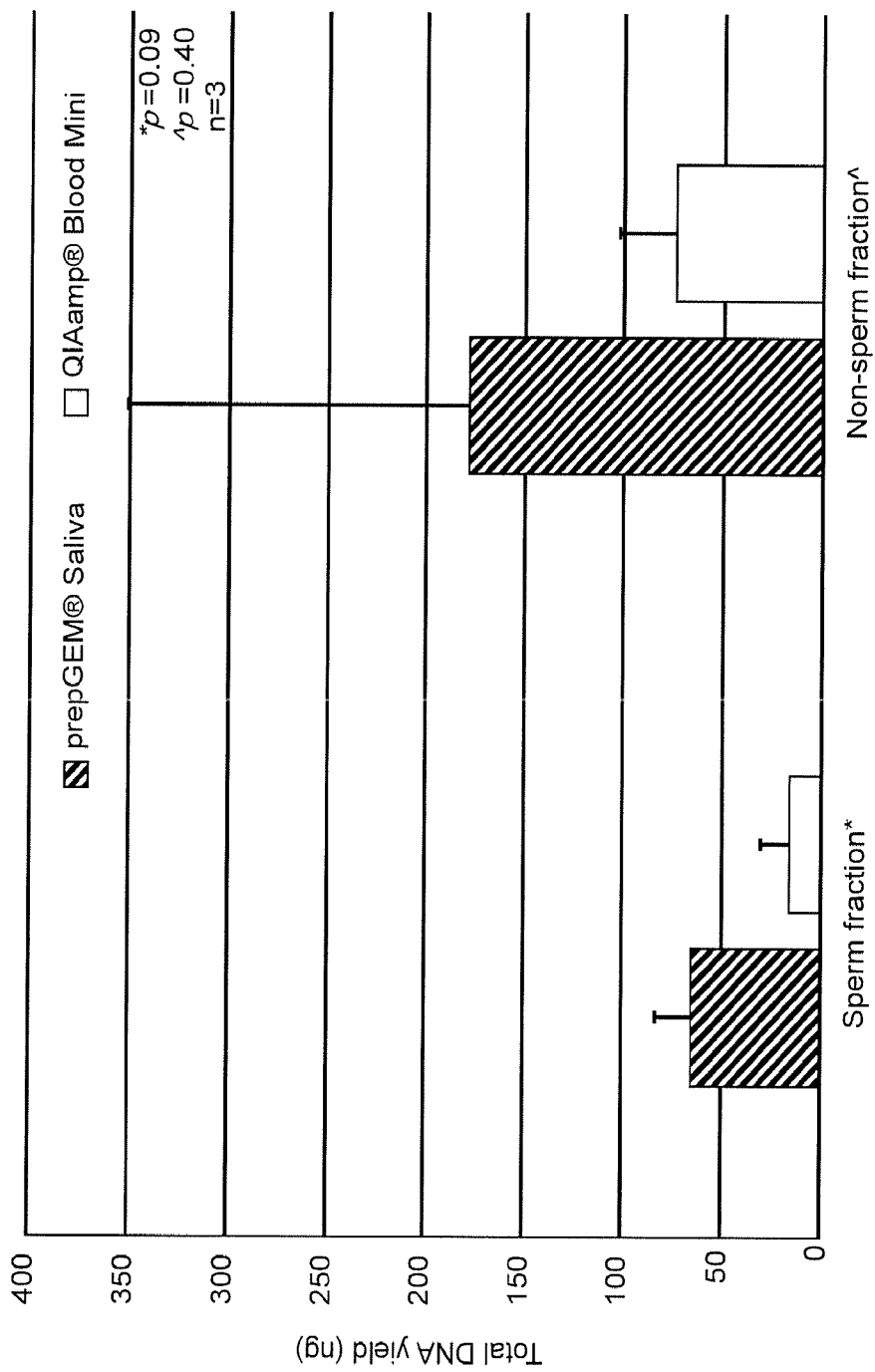
FIG. 3. DNA yields obtained from differential DNA extractions using a modified prepGEM® (a solution for extracting DNA available from VWR of Radnor, PA) method compared to a traditional differential method using QIAamp® (a DNA purification solution from Qiagen of Germantown, MD) DNA Blood Mini kit. prepGEM® resulted in a twofold increase in DNA in the non-sperm fraction, on average, versus the traditional method. More importantly, the prepGEM® modified method with added DTT resulted in a threefold increase in the DNA yield from the sperm fraction, on average, versus the traditional method. While not significant, these results show that the experimental modified differential prepGEM® method consistently improved the amount of DNA released and captured for amplification in both sperm- and non-sperm fractions thus indicating its suitability for integration into the sexual assault microdevice.

The proposed sexual assault microdevice architecture described above relies on the use of an enzyme-mediated DNA liberation assay. There are no reports of this method for use with sperm cells, which require special lysing conditions to disrupt the rigid acrosomal cap that protects the sperm cell head. Thus, a custom method was developed which uses a modified ZyGEM™ prepGEM® Saliva protocol. FIG. 3 shows the average DNA yield from both the sperm fraction and non-sperm fraction of the samples lysed and extracted with the modified ZyGEM™ prepGEM® Saliva and traditional lysis and QIAamp® extraction methods. Samples processed with the modified ZyGEM™ prepGEM® Saliva method had an average sperm fraction yield of 64.99±17.98 ng compared to QIAamp® DNA Blood Mini Kit at 15.75±14.48 ng (p=0.093). When comparing non-sperm fractions, samples processed with the modified ZyGEM™ prepGEM® Saliva method had an average yield of 178.1±172.6 ng whereas QJAamp® DNA Blood Mini Kit only contained only 73.85±28.47 ng on average (p=0.409). While not significant, these results show that the experimental modified differential ZyGEM™ prepGEM® can perform comparably to traditional differential lysis methods and is suitable for use with the disclosed sexual assault microdevice.

Antibody Evaluation Via Flow Cytometry

Figure 4:
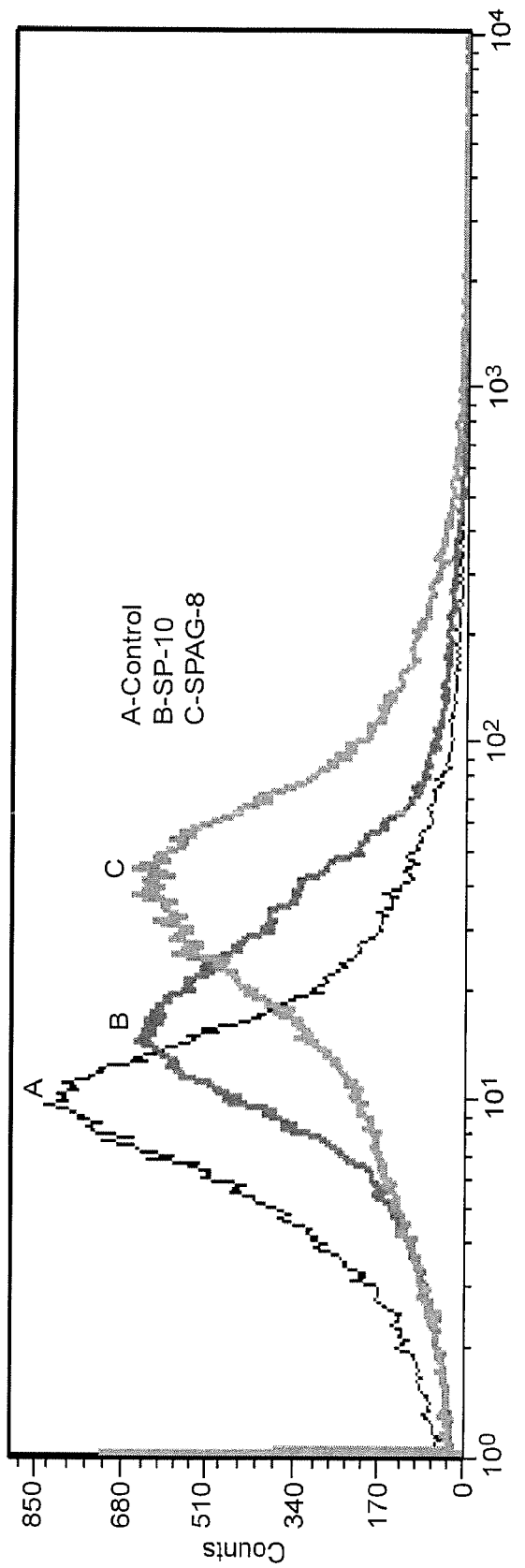
FIG. 4. Representative histogram from flow cytometry comparing the shift in fluorescence versus control using sperm antibodies SP-10 and SPAG-8 using an optimized protocol and rabbit IgG. This run was performed using a new seminal fluid flow cytometry cell preparation protocol with conditions for source body fluid volume, cell elution, wash conditions, and antibody concentration optimized and an Fc blocker additive (IgG) added to a pre-wash prior to antibody binding. A notable shift in fluorescence (FL4-H) was observed between cells incubated with the SP-10 antibody and the control, with significant overlap of fluorescence from antibody-bound events (cells) and the control fluorescence. However, a substantial shift was observed when cells were bound to the SPAG-8 antibodies, with a greater number of events (cells) bound to the fluorescent antibody falling completely outside of the control fluorescence. This indicates that the SPAG-8 showed a greater binding efficiency for the tested sperm cells with a majority of sperm cells present in the tested sample binding the SPAG-8 antibody (while only a portion of the sperm cells bound the SP-10).

A representative histogram of the antibody testing using the final optimized protocol is shown in FIG. 4. Peak A represents the isotype control, designed to show non-specific binding and establish a baseline for comparison. An improved binding efficiency was observed with this modified protocol (Peaks B and C, FIG. 4).

Figure 5:
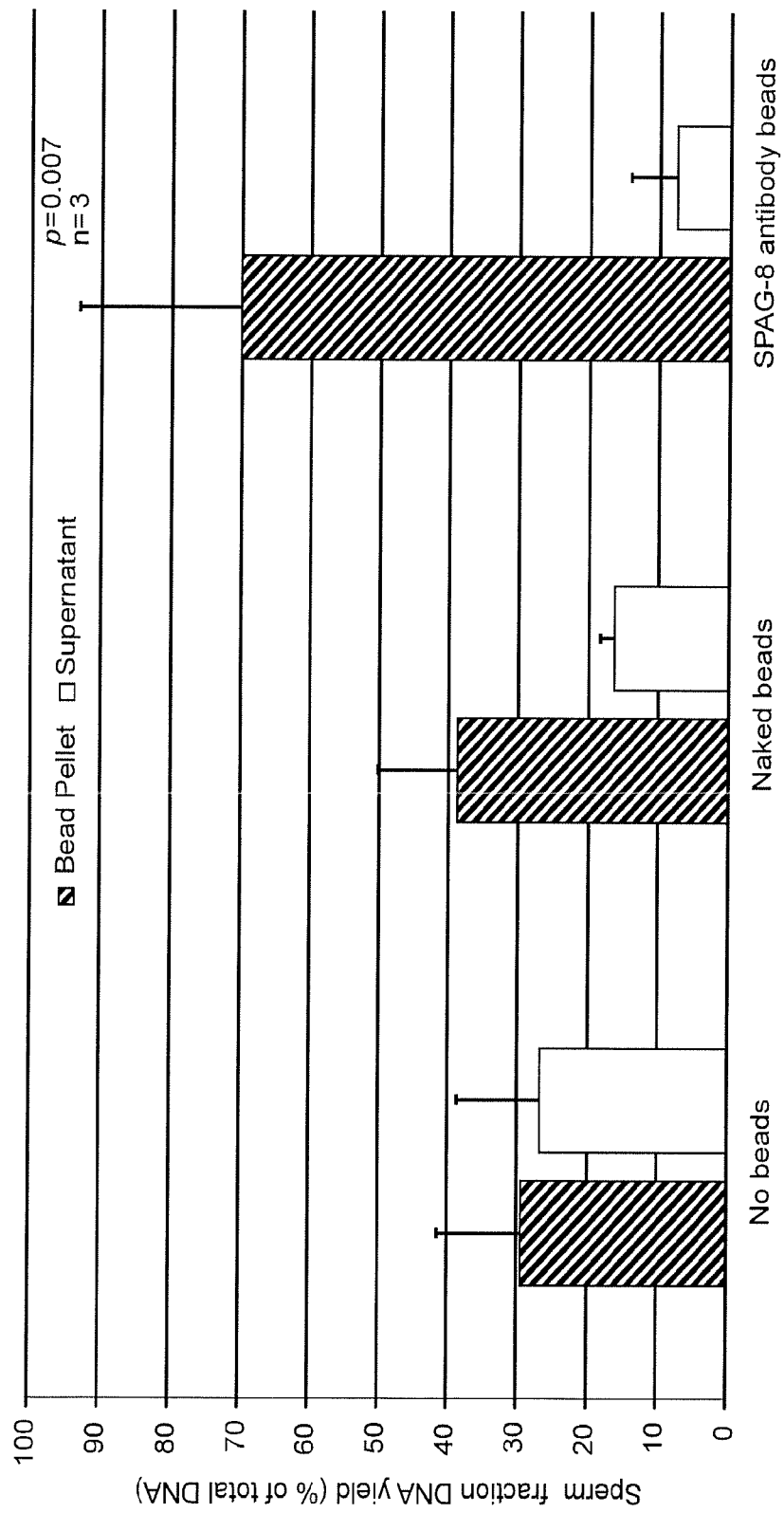
FIG. 5. Percent of total semen sperm fraction DNA yield in polystyrene bead pellet and supernatant for various conditions tested. These data show that approximately 60-75% of the cells in seminal fluid are sperm cells (DNA from sperm fraction), as expected. When no beads are added to the sample tested and samples are spun at a low speed (100×g), the DNA yield from the sperm fractions in the bead pellet and supernatant are approximately equal, indicating that half of the sperm are pelleted at the low pin and half are not. When the selected polystyrene beads (naked, no antibody) were incubated with seminal fluid and spun at the same low speed, no significant differences were observed, although the percent of sperm cells pelleting does slightly increase, on average, indicating that the added beads may be themselves responsible for trapping small number of additional sperm cells when pelleted at a low speed. When SPAG-8 antibody coated beads were added to the seminal fluid and spun at the same low speed, a significant increase in sperm fraction DNA yield was noted in the bead pellet, along with a similar decrease in sperm fraction DNA in the supernatant. Taken together, this data indicated that antibody-coated beads lead to a sharp increase in the number of sperm cells being captured by the low speed spin and that the majority of sperm cells present were capable of being captured by the beads coated with the SPAG-8 antibody.

The selected sperm antibodies were tested by flow cytometry using an optimized antibody binding/cell preparation protocol. Antibody SP-10 showed an average shift from control of 5.26±2.33% indicating that only a small portion of the antibodies were being bound to the target antigen (FIG. 5). However, antibody SPAG-8 showed an average shift from control of 19.72±12.16% (FIG. 5) (p=0.144). There are several reasons why these numbers are low and do not show more sperm binding when compared to the isotype control. First, the isotype control for these samples was more disperse than what is typically found. This could be due to the nature of the sample, the types of cells present, non-sperm target expression, or any extracellular material that may have persisted through the wash steps. This resulted in broadening of the control peak, which did not allow for full gating of the target cells. With a tighter isotype control this data may show better binding of sperm cells when compared to the control. While significant differences in binding between the two tested sperm-specific antibodies were not seen, the data did provide strong evidence that SPAG-8 consistently bound more sperm cells than SP-10. As such, SPAG-8 was used for the remainder of the antibody testing.

The MEA-1 male cell-specific antibody was evaluated by comparing the percent of positively stained cells from male buccal epithelial cells and sperm cells. The buccal epithelial cells showed on average 10.66±15.56% positively stained cells and the sperm cells had an average of 9.78±13.64% positively stained cells (Table 1) (p=0.960). The lack of significant differences between binding with these two groups indicates that this antibody could be acting in a male-specific manner, as desired. However, overall binding affinity is low (~10% of all male cells binding the antibody) and there was significant variation in binding efficiency between individuals when this antibody was used. The extreme variation noted among the three samples tested with this antibody is consistent with and could explain the contrasting results noted in the published literature that examine this antibody).

TABLE 1

Summary of DNA yields from the unbound and bound fractions from semen and vaginal swabs. $p > 0.05$ for all analyses

| Semen | | Vaginal | | Percent DNA Bound | |
|---|---|---|---|---|---|
| Bound DNA Yield (ng) | Unbound DNA Yield (ng) | Bound DNA Yield (ng) | Unbound DNA Yield (ng) | Semen | Vaginal |
| 10.82 ± 7.148 n = 3 | 22.47 ± 19.88 | 39.94 ± 30.56 n = 3 | 93.38 ± 95.19 | 36.91% ± 18.72 n = 3 | 35.96% ± 30.12 | p value > 0.05

Antibody Bead Complex Testing Off-Chip

Figure 6:
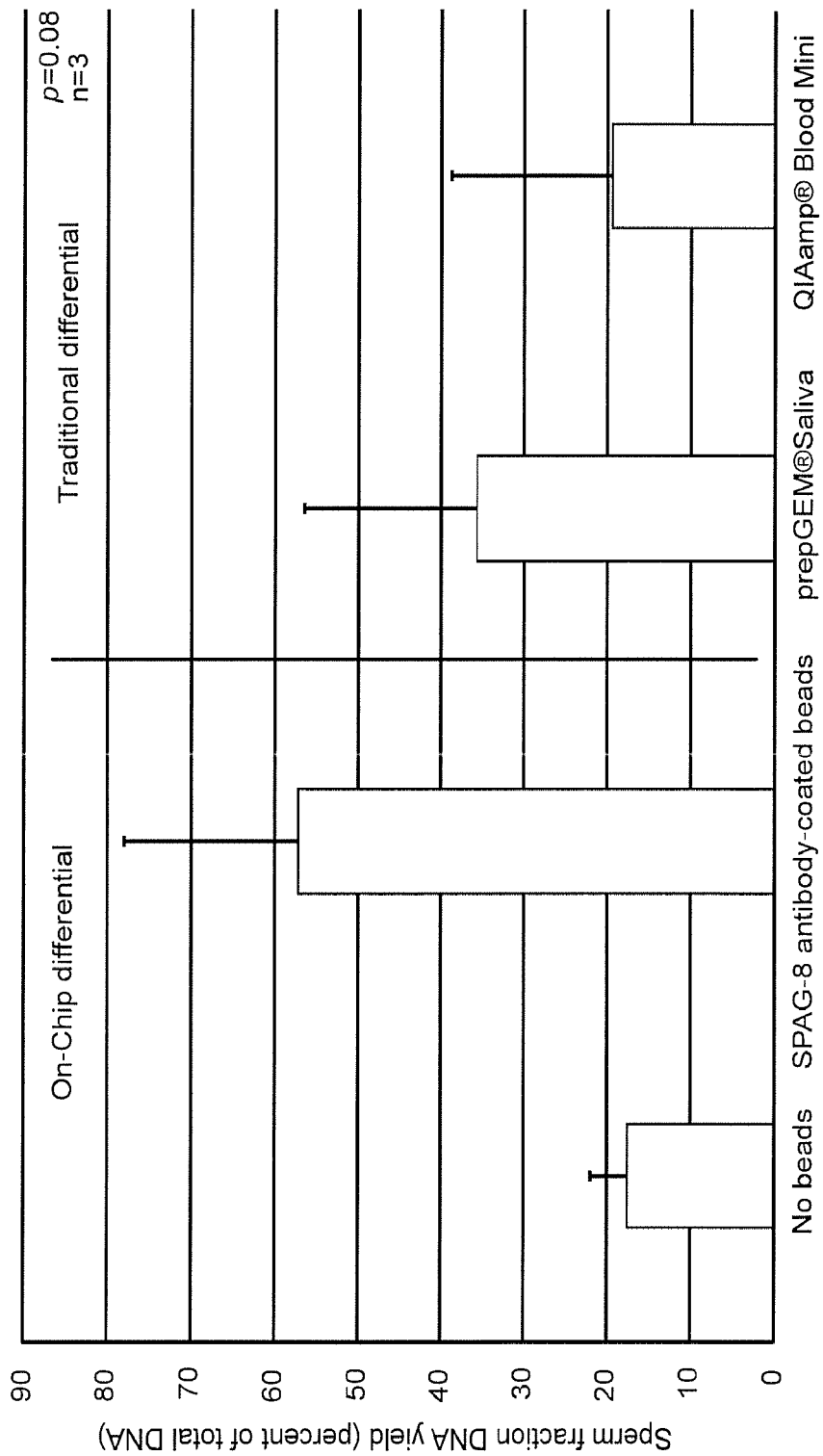
FIG. 6. Percent of total semen sperm fraction DNA yield from the bead pellet using on-chip antibody-coated beads to capture sperm cells versus traditional differential methods. The SPAG-8 antibody-coated beads tested on-chip using the simple chip design and the modified prepGEM® method yielded, on average, more sperm DNA in the bead pellet than the sperm fractions from traditional differential lysis and DNA purification methods. This data, along with the observed increase in total DNA yields using the antibody-mediated chip based method (data not shown), indicates that the SPAG-8 antibody-coated bead mechanism used on a microchip device is capable of more successfully binding, and thus, separating sperm cells than traditional differential methods.

With the selection of SPAG-8 as an initial sperm-specific antibody for the proposed microdevice, the efficiency of the binding using the proposed bead-mediated mechanism was tested. After incubation of semen samples with the SPAG-8 antibody-coated polystyrene beads, tubes were spun down so that DNA yields from the bead pellet (bound cells) could be was compared to those from the supernatant (unbound cells). The amount of the total sample DNA that was obtained from the sperm fraction of the bead pellet and the sperm fraction of the supernatant were approximately equal when no beads were added and the sample indicating that half of the sperm cells are naturally pelleted at the low speed spin and half were not (FIG. 6). When the polystyrene beads (naked, containing no antibodies) were incubated with the same seminal fluid samples and spun at the same low speed, no significant differences were noted although the percent of sperm cells pelleting does slightly increase (FIG. 6). This could indicate that the polystyrene beads themselves may be responsible for trapping a small number of sperm cells when pelleted at a low speed. However, when the SPAG-8 antibody-coated beads were tested with the same semen samples and spun at the same low speed, a significant increase in sperm fraction DNA yield was noted (70.09±22.96% of the total DNA) along with a similar decrease in sperm fraction DNA isolated from the supernatant (only 7.59±6.61%) (FIG. 6, p=0.007). These data indicate that SPAG-8 antibody-coated beads are capable of successfully and significantly enriching for the selection of sperm cells when compared to sperm cells left unbound in the supernatant fraction (p=0.0007) and as compared to the sperm cells captured when no beads are used at all (p=0.020).

Antibody Bead Complex Testing On-Chip

In order to test the effectiveness of the SPAG-8 antibody-bead based mechanism for sperm and non-sperm separation in a microchip environment, a simple single module microdevice was developed that included only an inlet reservoir and an outlet reservoir separated by a mechanical valve (FIG. 2A). This simple design presented an easy way to test both antibody-coated bead binding on-chip and the ability of the antibody-bead-sperm cell complex to subsequently move successfully through a valve in a chip made of materials identical to those proposed for use with the new sexual assault microdevice. For this test, SPAG-8 antibody-coated polystyrene beads were incubated with seminal fluid directly in the simple microdevice, using procedures identical to those used for binding in off-chip studies. Use of the SPAG-8 antibody-coated beads resulted in a 39% increase in the amount of sperm cell DNA captured in the microchip environment when compared to incubation of the same samples without antibody-coated beads (FIG. 6). When compared to results obtained off-chip using a traditional differential lysis and DNA extraction methods, a significant increase in the amount of sperm cell DNA captured was also observed (FIG. 6, p=0.080).

Sexual Assault Microdevice Testing

After the bead-antibody complex showed satisfactory binding of sperm cells in the simple microdevice environment, testing was moved onto the integrated sexual assault microdevice. As described above, the testing was performed on cuttings from semen, vaginal, and mock post-coital (a combination of semen and vaginal) swabs. The DNA yields of the bound and unbound fractions from the sperm and vaginal samples are shown in Table 1. The unbound fraction DNA yield for both sperm and vaginal samples were over twice that of their respective bound fraction yields on average.

Figure 7:
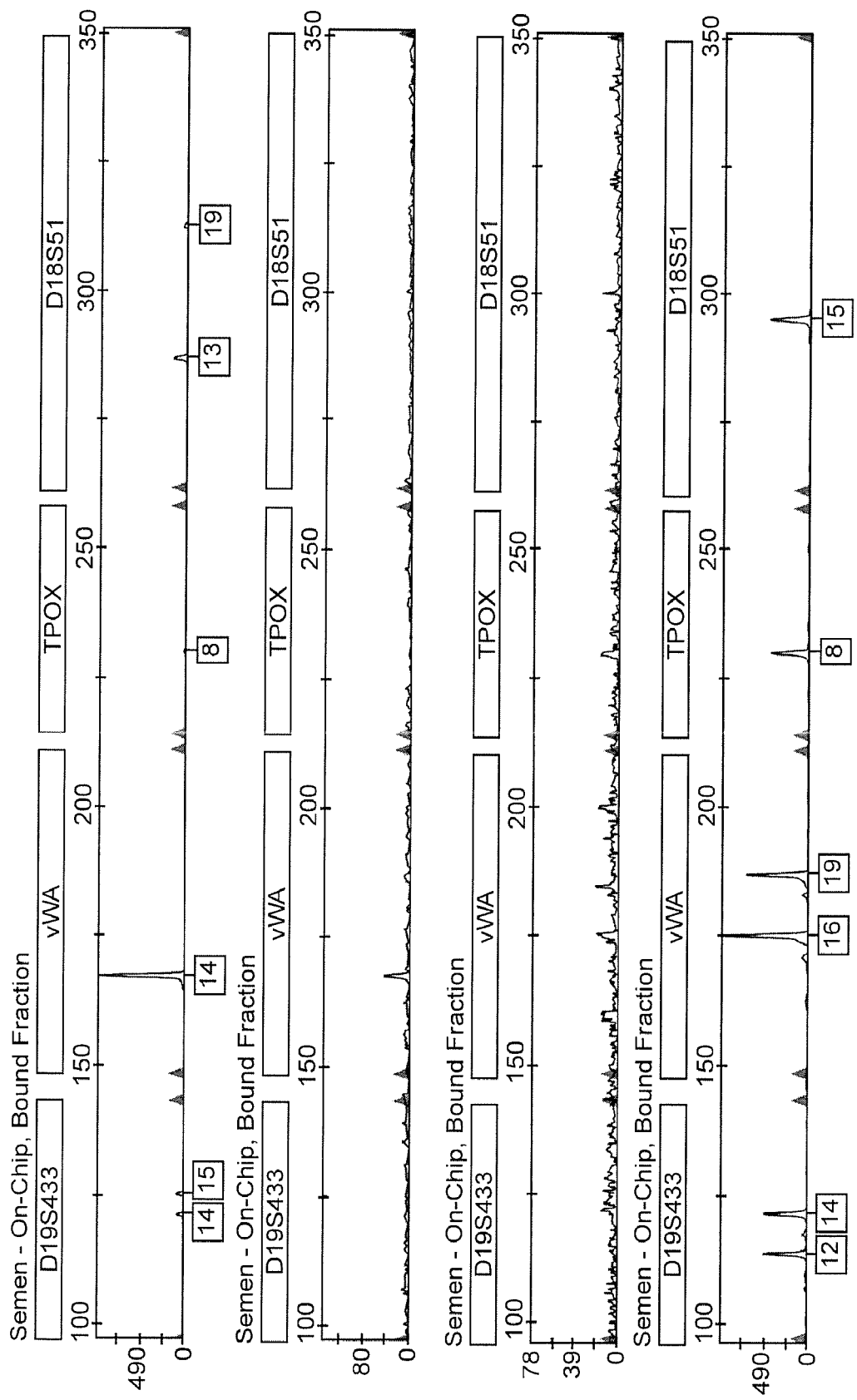
FIG. 7. Electropherogram screenshots of the yellow channel for on-chip semen and vaginal samples. The bound fraction completely enriched in the semen sample, while the unbound fraction completely enriched in the vaginal sample.

However, STR profiles from the semen and vaginal samples do not seem to support the quantitative data. Although the unbound fraction of the semen samples contained an average of 22.47 ng of DNA, representative STR profiles show peaks only in the bound fraction (FIG. 7). The inverse is also true of the vaginal samples: Although their bound fraction contained an average of 39.94 ng of DNA, representative STR profiles show peaks only in the unbound fraction.

Figure 8:
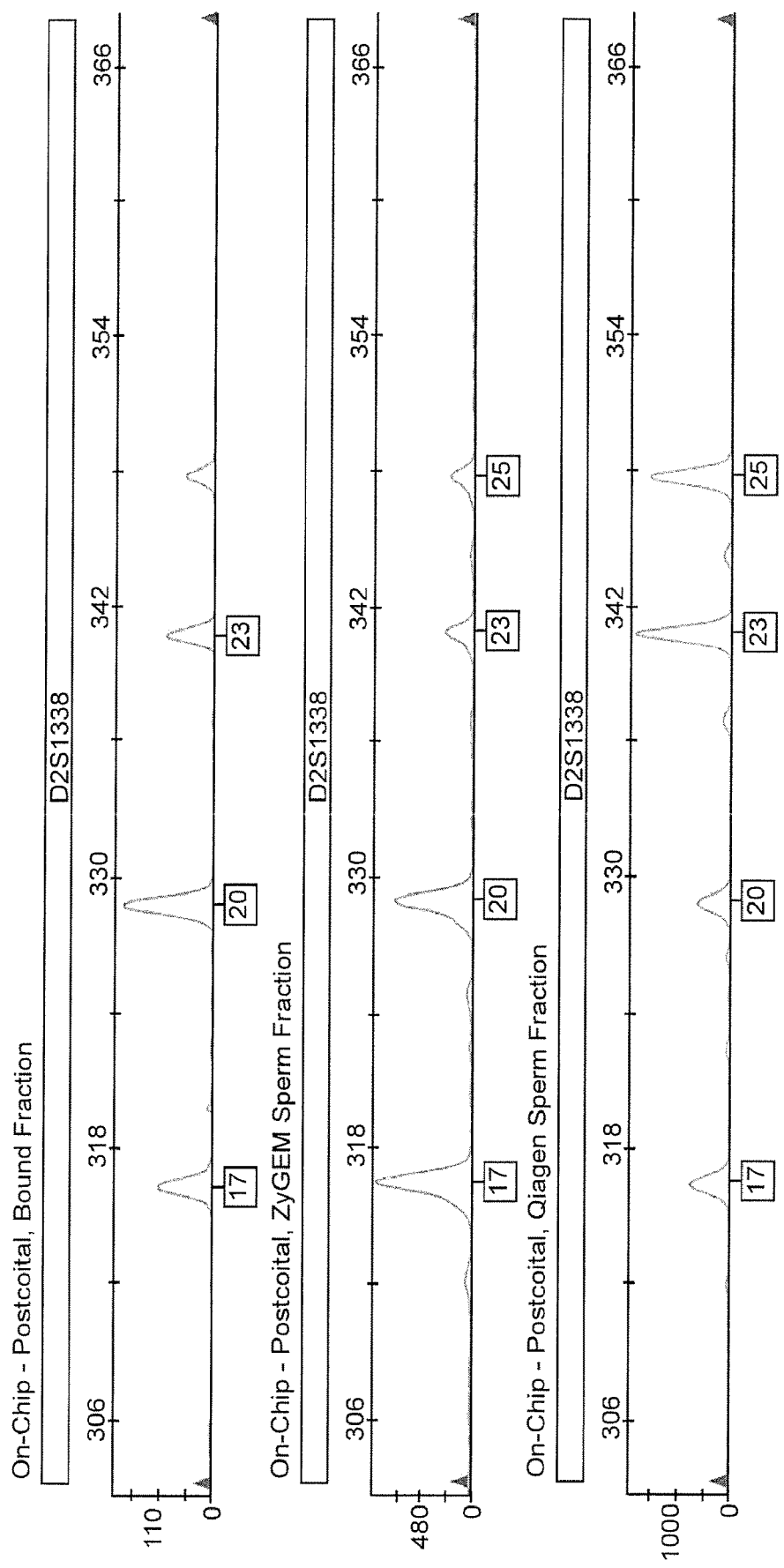
FIG. 8. Electropherogram screenshots of the D2 locus in the green channel for bound/sperm fractions of mock post-coital samples. The on-chip antibody-mediated separation shows a better separation and enrichment for the male (23,25) DNA (3:1 vs. 4.5:1 female:male) than the off-chip ZyGEM differential extraction, but not as strong as the traditional Qiagen differential extraction (1:3.5).
Figure 9:
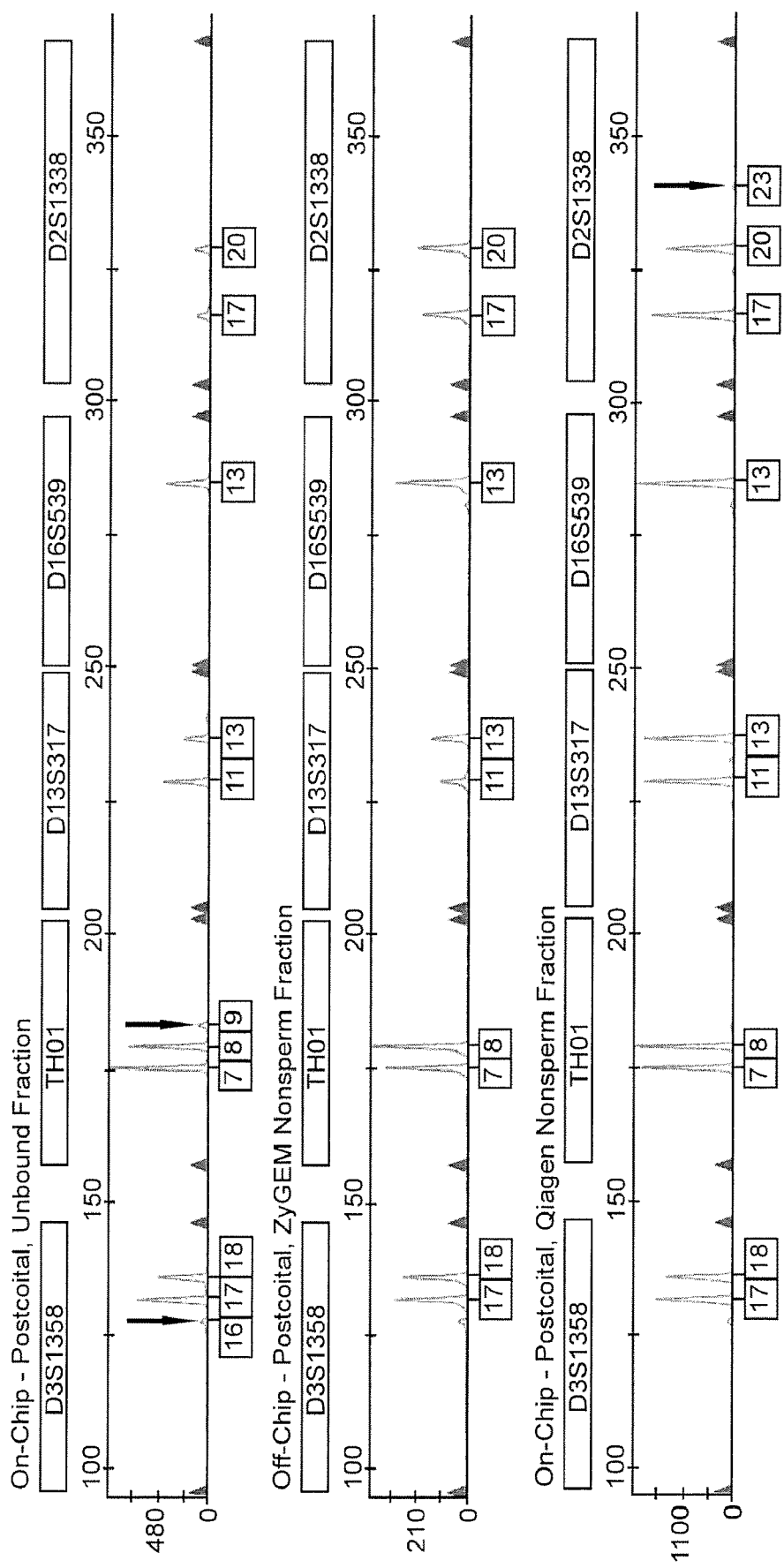
FIG. 9. Electropherogram screenshots of the green channel for unbound/nonsperm fraction of mock postcoital samples. All three methods show a clear major female profiles with >10:1 female:male peak height ratios (17:1, no male, and 28:1 respectively). Arrows indicate unique minor contributor (male) alleles.

To further test the effectiveness of the on-chip cell separation, STR profiles from three groups (on-chip separation, off-chip ZyGEM differential extraction, and off-chip Qiagen differential extraction, each performed on the same post-coital samples) were compared. In the bound (for on-chip) and sperm (for off-chip) fractions, the on-chip method produced a female:male peak height ratio of 3:1, which showed better enrichment of the male fraction than the off-chip ZyGEM differential (4.5:1). However, it did not enrich for the male fraction as well as the traditional Qiagen differential method, which gave a female:male ratio of 1:3.5 (FIG. 8). In the unbound (for on-chip) and non-sperm (for off-chip) fractions, all three methods showed very clear female profiles, with little-to-no male sample detected (FIG. 9). While this shows that the antibody-bead complex does seem to bind most of the sperm cells in the post-coital sample, the complex also seems to bind too many female cells as well.

CONCLUSIONS

The sexual assault microdevice advantageously offers a closed-system solution to specific work flow processes, reducing the opportunity for contamination. Additionally, the availability of a simple, automated microdevice for front-end processing of sexual assault swab samples significantly reduces the amount of hands-on analyst time spent with evidence samples from sexual assault cases. This frees analysts' time for other tasks, including data interpretation and reporting of results. This becomes even more important with sexual assault cases, as they typically involve mixtures, which require additional analyst training and skill as well as additional interpretation time. Shifting a lab's human resources to the more important downstream tasks allows cases to be reported more quickly, which would ultimately help relieve the ever-growing backlog of sexual assault cases in the United States. Secondly, the proposed microdevice offers a faster solution to differential cell lysis and extraction, reducing the time associated with this step of the workflow from approximately four hours to one hour versus traditional methods.

The described sexual assault microdevice offers many other potential advantages to traditional, manual differential lysis and extraction methods. For example, as this device seeks only to replace the differential cell lysis, DNA extraction, and multiplex STR amplification steps (and not the back-end CE and data interpretation methods), the validation and training time needed for implementation of this device would be minimal. This microdevice provides amplified STR product that can be easily removed and onto conventional capillary electrophoresis instruments using standard analysis software with standard default settings. Additionally, this device offers a simple, robust approach that is easy to use, which reduces the training time associated with differential lysis and DNA extraction, thus offering additional time savings. These time savings, coupled with the low cost of the materials, reagents, and associated microdevice hardware results in significant overall cost savings to a forensic DNA laboratory. Further cost savings are achieved with a small increase in the size of the microdevice to accommodate multi-sample processing. Ultimately, when this microdevice and its associated microfluidic control mechanisms are incorporated into a single commercial sexual assault differential extraction and amplification device, the resulting instrument is very small. Thus, an inexpensive solution with a small footprint is offered, which also improves the potential for portability.

Example 2. A Microchip Module for Antibody-Mediated Differential Separation of Non-Seminal Male/Female Mixtures from Sexual Assault Samples With many sexual assault cases, circumstances arise that lead to an absence of sperm cells and/or seminal fluid. These circumstances include assaults that involve licking or sucking of the victim, vasectomized male assailants, and/or touch cases, from which only epithelial cells are shed from the assailant. This Example describes testing of a microdevice for the differentiation of multiple epithelial cell types present in non-sperm containing sexual assault samples.

Methods and Materials
Sample Collection

Buccal swabs, hand epithelial swabs, and penile epithelial swabs were collected from three males. In addition, breast epithelial, vaginal, and vulval samples were collected from three females. Samples processed on the sexual assault microdevice were collected using foam swabs (Fisherbrand™, Pittsburgh, PA), and the samples for all other tests in this study were collected using cotton swabs (Evident™, Union Hall, VA). Since penile, hand and breast epithelial cells are shed from contact, the double-swab technique with ddH$_2$O was used for collection. When swabbing the vulva, the volunteers were instructed to only swab the outside of the vagina (the lip/lip area) and not the vaginal canal. Lastly, all vaginal and vulval samples were collected within seven days after sexual activity. All swabs were stored at 4° C. until processing. All samples collected were in accordance with the VCU approved IRB protocol HMW20002942.

Antibody Selection

Categories of varying sexual assaults were developed to facilitate identification of antibodies that may be used to target and select for particular cell types. The first category includes mixtures of saliva/buccal epithelial cells, such as what may be expected if an assailant orally assaults a victim. Antibodies were identified that target proteins on the cell surface of these cell types, and thus could separate cells shed by a mucous membrane from skin epithelial cells. The second category includes mixtures of vaginal epithelial cells with shed keratinized skin epithelial cells such as what may be expected when an assailant penetrates (digital or penile) the victim's vaginal cavity but does not ejaculate.

A comprehensive literature search was conducted to identify antibodies that could allow for enrichment of male or female-specific cells as well as cells from specific non-sperm sexual assault samples [touch epithelial cells (breast, penile, and hand), buccal epithelial cells, vaginal epithelial cells, and vulval epithelial cells]. Candidate antibodies for each cell type were ranked based on the following characteristics: high expression of the target antigen on the cell membrane of the targeted cell population, the longevity of the antigen's expression on the cell membrane, expression solely in male or female epithelial cells, and tissue specific expression if multiple epithelial cell types were present.

Lists were generated for each sexual assault category (Tables 2 and 3). These lists rank the identified antibodies based on their species specificity, expression level on the cell membrane, cross-reactivity with other known antibodies, availability for purchase, and expected cell target.

TABLE 2

Antibodies identified to target epithelial cells in instances where sucking, licking, and biting occurred in a sexual assault.
Oral-body assault

| Rank | Antibody | Species specificity | Cell target | Expression level | Target Antigen Location | Cross reactivity |
|---|---|---|---|---|---|---|
| 1 | SPRR2 | Human | Buccal epithelium | High | Cell membrane | None known |
| 2 | Cytokeratin 4 | Human | Buccal epithelium | High | Cell membrane | Present on vaginal epithelial cells |
| 3 | CD36 | Human | Gum epithelium | High | Cell membrane | None known |
| 4 | Cytokeratin 10 | Mouse, rat, human | Skin | High | Cell membrane | None known |
| 5 | Collagen XVII | Sheep, goat, horse, cow, pig, guinea, human | Skin | High | Cell membrane | None known |

TABLE 3

Antibodies identified to target epithelial cells in instances where vaginal penetration without ejaculation occurred in a sexual assault
Penetration without semen

| Rank | Antibody | Species specificity | Cell target | Expression level | Target Antigen Location | Cross reactivity |
|---|---|---|---|---|---|---|
| 1 | LH 39 | Human | Vaginal epithelium | High | Cell membrane | None known |
| 2 | Laminin 1 | Human | Vulval skin | High | Cell membrane | None known |
| 3 | Cytokeratin 4 | Human | Vaginal epithelium | High | Cell membrane | Buccal epithelium |
| 4 | Betadefensin 2 | Human | Human Skin and oral epithelium | High | Cell membrane | None known |
| 5 | Cytokeratin 10 | Mouse, rat, human | Skin | High | Cell membrane | None known |
| 6 | Collagen 17 | Sheep, goat, horse, guinea pig, cow, human | Skin | High | Cell membrane | None known |
| 7 | Cornulin | Human | Foreskin | High | Cell membrane | None known |

The antibodies that were chosen for the oral-body assaults category were Cytokeratin 4 and SPRR2. The antibodies that were chosen for the penetration without semen category were Cytokeratin 4 and Laminin-1.

Antibody Evaluation Via Flow Cytometry Testing

Three FITC-labeled (fluorescent) antibodies were selected for testing: Cytokeratin 4 (CUSA Bio, College Park, MD), Laminin-1 (Bioss, Washburn, MA), and SPRR2 (LS-Bio, Seattle, WA). Antibody-binding efficacy was initially tested against samples of the targeted cell type and on samples of non-targeted cell types present in the mixture (n=3). Therefore, Cytokeratin 4 was tested against buccal, vaginal, hand, and breast cells; Laminin-1 was tested against vaginal, vulval, and penile epithelial cells; SPRR2 was tested against to breast and buccal epithelial cells. For binding, swab samples were eluted in 400 μl of PBS (Quality Biological, Gaithersburg, MD) at 37° C. for 2 hr. vortexing every 15 min. Next, the swab was removed and 200 μl of the eluate was moved to a separate isotype control tube for staining. When the samples were ready to be stained with the antibody, the eluate was spun down at 400×g for 5 min. and the supernatant was removed, which was followed by resuspension in 300 μl of cell staining buffer (Southern Biotech, Birmingham, AL). This process was repeated twice more for a total of three washes.

Next, in order to block the non-specific antibodies expressed on the cell membrane, 25 μl of a 0.16 mg/ml solution of rabbit IgG (GenScript, Piscataway, NJ), as well as 5 μl of FcR Blocker (Miltenyi Biotec Inc., San Diego, CA), was added. The sample tubes were then wrapped in foil and placed in 4° C. for 10-20 min. Following the blocking step, 25 μl of a 20 ng/μl solution of the antibody (either the isotype control or the targeted antibody) was added to each sample, and the sample tubes were again wrapped in foil and placed in 4° C. for 35 min. After staining, the cells were spun down at 400×g for 5 min, the supernatant was removed, and the cells were resuspended in 300 μl of cell staining buffer. This process was repeated two more times, for a total of three washes. Lastly, the cells were resuspended in 200 μl of cell staining buffer and pipette through a nylon mesh strainer. The samples were then run on the FACSCelesta™ flow cytometer (BD Biosciences, San Jose, CA). The forward scatter was set to 181 fluorescent units and the side scatter was set to 165 fluorescent units. In order to capture the stained cells in the targeted cell population, a gate was set based on the granularity and the size of the cell. The run was stopped either after 100,000 cells were detected or after 45 sec. All Cytokeratin 4 samples were tested in duplicate, whereas Laminin 1 and SPRR2 samples were tested in triplicate. A threshold was set on the isotype control, to which positively stained samples were compared, thus generating a value of the percentage of cells in the gated cell population that stained positive for the antibody. The isotype control fluorescence value was subtracted from the positively stained samples, and these values for all samples in the targeted cell population were averaged. An analysis of variances (ANOVA) statistical test was performed on these averages, which was coupled with Tukey HSD post-hoc analysis when the p-value was significant (a=0.05).

Antibody Testing Using Bead-Mediated Binding in a Microcentrifuge Tube

Streptavidin-coated polystyrene beads were used in this study. To bind the antibody to the polystyrene beads, 9 μl of beads (Spherotech, Lake Forest, IL) per sample tested was suspended in 1 mL of PBS. The beads were washed three times in 1 mL of PBS and were spun at 100×g for 60 sec. Next, depending on the targeted cell type, 0.167 μg/sample of biotinylated Cytokeratin 4 (CUSA Bio), Laminin-1 (Bioss), or SPRR2 (LSBio) was added to the beads, and they were incubated at room temperature for 30 min. with gentle vortexing every 30 sec. Following binding, the beads were washed five times in 1 mL of PBS and spun at 100×g for 60 sec. Lastly, the beads were resuspended in 9 μl of PBS per sample. For elution of the buccal (n=5), vulval (n=3) and vaginal (n=5) cells off of the swab, 200 μl of PBS was added to each sample followed by incubation at 37° C. for 2 hr. with vortexing for 10 sec. every 15 min. The antibody-bead complex (described above) was then added to 10 μl of each sample in a 0.2 ml tube, and the samples were incubated at room temperature for 35 min.

Before incubation, the samples were spun for 60 sec. at 100×g, and the supernatant was removed to separate the sample into bound and unbound fractions. Next, a modified ZyGEM™ prepGEM™ (ZyGEM™, Hamilton, New Zealand) extraction protocol was followed to lyse cells and liberate DNA from both fractions. Lastly, to ensure the polystyrene beads did not interfere with quantification, the bound fraction sample tubes were spun down at 100×g for 60 sec. All samples were tested in triplicate. DNA was quantified from each sample using the Qiagen Investigator Quantiplex® HYres kit (Qiagen, Valencia, CA) on an Applied Biosystems™ 7500 Real Time PCR System (Life Technologies, Foster City, CA) following the manufacturer's protocol, but using half reactions. Quantification data were analyzed as described below.

Antibody Testing in a Plastic (PMMA) Microdevice

The antibody-bead mechanism was then tested in a poly (methyl methacrylate) (PMMA) microdevice to confirm the chemistry works with reduced volumes and that the complex does not interact with the chip. The binding efficacy of antibodies was tested in an enclosed plastic (PMMA) microdevice environment. This simplified chip included an inlet port, a binding chamber, a mechanical valve, and a storage chamber. The antibody-bead complexes used in this testing were prepared as described above.

Buccal (n=5), vulval (n=3), and vaginal (n=5) samples were eluted off the cotton swab as described above. Next, 10 μl of sample was incubated with the antibody-bead complex (9 μl) in the antibody binding chamber for 35 min. at room temperature. To move the unbound sample to the storage chamber, the chip was spun at approximately 1100 rpm for 60 sec. Samples were removed from the antibody-binding chamber (bound fraction) and storage chamber (unbound fraction) and placed in 0.2 ml tubes. Cell lysis and DNA liberation followed, using a modified ZyGEM™ prepGEM™ saliva extraction protocol. DNA from both fractions were then quantified with the Qiagen Investigator Quantiplex® HYres kit following the manufacturer's protocol, but using half reactions on an Applied Biosystems™ 7500 Real Time PCR system. Quantification data were analyzed as described below.

Microdevice Design, Fabrication, and Instrumentation

Figure 10:
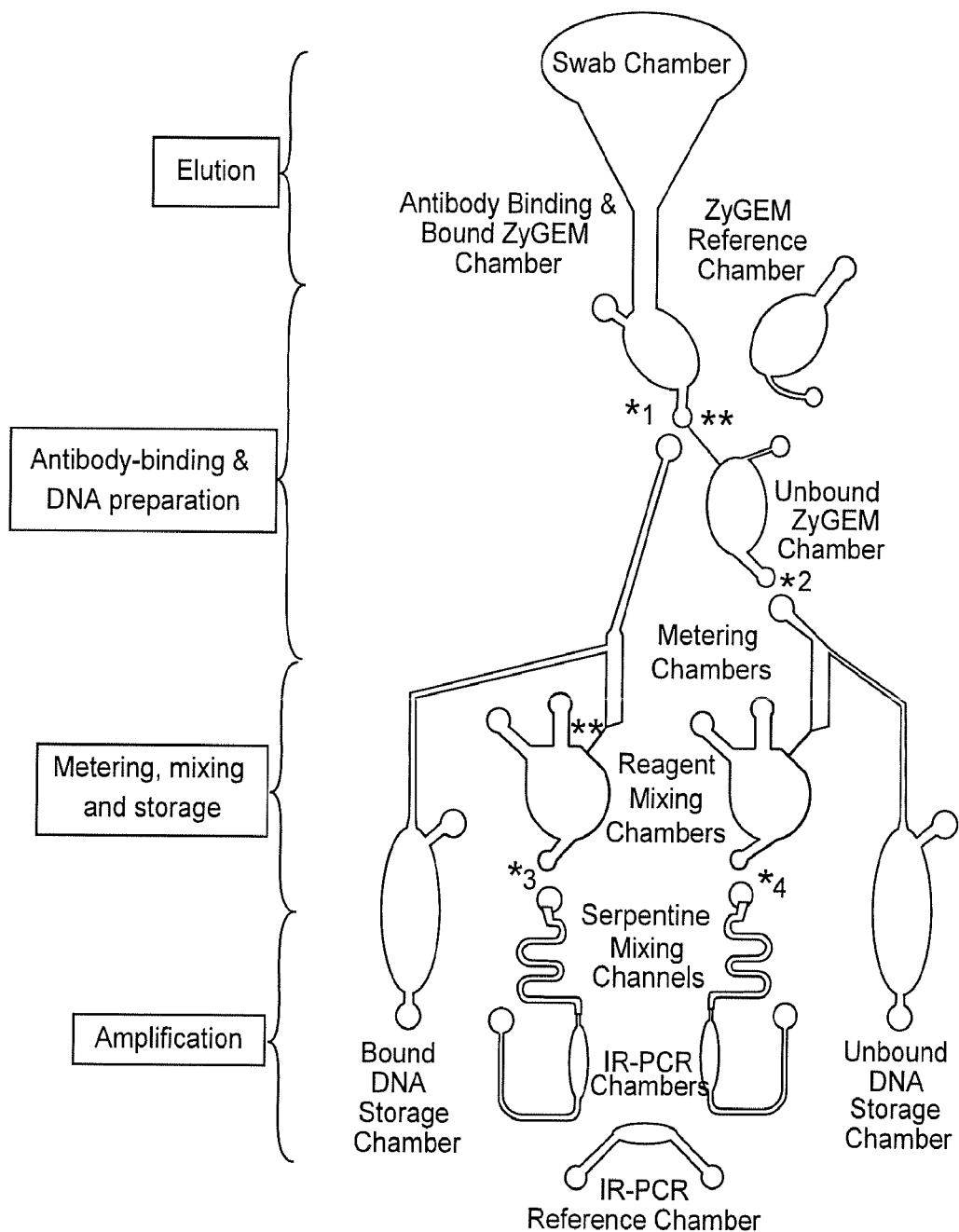
FIG. 10. Exemplary modified sexual assault microdevice. In this schematic representation, the holding chamber (depicted in Figure B) has been eliminated.

Modifications to the sexual assault microdevice architecture were done using AutoCAD LT® 2004 software (Autodesk®, San Rafael, CA). Modifications included the removal of a chamber and moving the reference chamber (FIG. 10). These designs were then exported to the VLS 3.5 software, which interfaces with the VersaLaser® $CO_2$ laser ablation instrument (Universal Laser Systems, Scottsdale, AZ). This instrument was used to cut 0.5 mm and 1.0 mm layers of PMMA for the top/bottom and middle layers, respectively. The microdevice layers were then thermally bonded. The coupling of the modified centrifugal apparatus with the burst and mechanical valves controlled the movement of fluid between the compartments in the microdevice. Lastly, for DNA liberation on the sexual assault microdevice, this work made use of an IR-PCR instrument.

Antibody Testing in the Separation Module of the Sexual Assault Microdevice

Sample preparation included the development of mock case samples depending on the sexual assault scenario: breast and buccal samples were combined to generate mock oral-body assaults, whereas penile and vaginal, and penile and vulval samples, were combined to generate mock penetration without ejaculation assault samples (n=3). Initially, samples were eluted in 200 μl of PBS at 37° C. for two hr. with vortexing 10 sec. every 15 min. To pellet the cells, samples were spun down at 400×g for 4 min and the supernatant was removed. Then, 50 μl of PBS was added to each sample, the samples were vortexed, and then the samples were combined together in one tube to generate the desired mixtures. Foam swabs were then dipped in the sample, ensuring that the entire swab was covered, and then they were dried overnight. In addition to the mixture swabs, neat breast, buccal, vaginal, vulval and penile swabs (n=3)

were cut as controls in one-sixth fragments and stored in 4° C. until processing on the modified sexual assault microdevice (FIG. 10).

Prior to processing on the sexual assault microdevice, modifications to the ZyGEM™ master mix and bead-washing steps needed to be completed. First, to minimize the potential for premature lysis by the ZyGEM™ enzyme, and considering the volume of liquid on the microdevice is limited, the antibody-bead complex was resuspended in 4 ul of sterile water per sample instead of in 9 μl of PBS per sample, which had been used previously. In addition, the ZyGEM™ prepGEM™ master mix was also modified to account for the limited amount of space in each chamber. Two separate master mixes were made for both the bound and unbound fractions: the bound fraction contained 0.24 μl of ZyGEM™ prepGEM™, 10.56 μl of sterile water, and 1.41 of 10× Blue Buffer, whereas the unbound fraction contained only 0.24 μl of ZyGEM™ prepGEM™ and 1.41 of 10× Blue Buffer. Microdevice processing began by eluting cells from the foam swab in the swab elution chamber with 14.56 μl of sterile water. This was done by agitating the swab, followed by a brief spin on the modified centrifugal apparatus at approximately 345 rpm for 60 sec. Next, 4 μl of the antibody-bead solution was added to and mixed with the sample in the antibody binding chamber. The sample was incubated at room temperature for 35 min. Following incubation, the chip was spun on the modified centrifugal apparatus for 60 sec. at 700 rpm, allowing the cells not bound to the polystyrene beads to move to the unbound ZyGEM™ chamber via the burst valve. Considering approximately 8 μl of swab eluate was present and the beads were suspended in 4 μl of sterile water, only the 10× Blue Buffer and the ZyGEM™ prepGEM™ components of the master mix were added to the unbound ZyGEM™ chamber. However, 12 μl of the bound ZyGEM™ master mix was added to the antibody binding/bound ZyGEM™ chamber. Next, the thermocouple and 12 μl of sterile water were added to the reference chamber, and the manifold was reassembled for DNA liberation on the IR-PCR device at 75° C. for 3 minutes. After DNA liberation, the bound and unbound fractions were removed and placed in separate 0.2 ml PCR tubes. These samples were quantified using the Qiagen Investigator Quantiplex® HYres kit as described above. Next, 5 μl of sample was amplified using the AmpFCSTR™ Identifiler™ PCR Kit (ThermoFisher Scientific, Rochester, NY), which contained AmpFCSTR™ PCR reaction mix (5.70 μl), AmpFCSTR™ Identifiler™ Primer Set (2.00 μl), TE-4 (2.10 μl), and AmpliTaq Gold DNA polymerase 5 U/μl (0.20 μl). The samples were run on a ProFlex™ PCR System (Life Technologies, Foster City, CA) with the following parameters: 1 cycle of 11 min. at 95° C., followed by 28 cycles for 1 min. each of 94° C., 59° C., and 72° C., and a final extension step at 60° C. for 90 min. After amplification, samples were analyzed using the Applied Biosystems™ 3130xl genetic analyzer (Applied Biosystems™, Foster City, CA) with Data Collecton software version 3.1 (ThermoFisher Scientific) following manufacturer recommendations. For this, 1.2 μl of amplified sample was added to 12.0 ul of Hi-Di formamide and 0.1 μl of GS 500-LIZ (Life Technologies) per sample. A 36 cm capillary array (Thermofisher Scientific), and POP-4® polymer (ThermoFisher Scientific), were used along with a standard 10 s 3 kV injection). GeneMapper™ version 4.1 (ThermoFisher Scientific) was used for visualization of results and data review. Data analysis was performed as described below.

Data Analysis

To analyze the data generated from quantification for the in-tube and simple microdevice testing, the total yield of DNA that was liberated from cells bound to the beads and the total yield of DNA that was unbound were calculated by multiplying the concentration (ng/μl) by 100. Next, using this value the percent of total DNA bound and the percent of total DNA unbound was calculated. DNA quantification data from bound and unbound fractions were compared using an analysis of variance (ANOVA) coupled with Tukey HSD post-hoc analysis when the p value was significant (a=0.05). Lastly, to analyze the STR data from the separation module testing on the sexual assault microdevice, the allele calls and relative fluorescent units (rfu) were recorded at each locus. The alleles for the clean mock case samples were compared to the known reference profile and then to the mixture in which they were present. The total number of alleles observed for each sample tested were recorded; artifacts observed were documented. Major:minor ratios were then generated from the mixture samples by dividing the minor peak heights by the total peak heights at each locus and then taking the reciprocal of this value.

Oral-Body Assaults

Antibody Evaluation Via Flow Cytometry

The binding efficacy of the selected antibodies on the targeted cell membrane antigen was assessed via flow cytometry. The selectivity of Cytokeratin 4 was tested with the targeted cell types (buccal and vaginal cells), as well as the other cell type presumed present in a non-sperm sexual assault mixture (breast and hand epidermal epithelial cells). Considering Cytokeratin 4 can be used for both categories, the results from each category will be discussed separately. For the oral-body assault category, mixtures of buccal cells and breast epidermal cells were stained with Cytokeratin 4, and an average of 64.88%+16.95 of buccal cells were bound, whereas only 0.803%+8.450 of breast epithelial cells were bound (p<0.0001) (not shown). Cytokeratin 4 binding on buccal and vaginal epithelial cells is 80 and 6.5-fold higher than breast and hand epithelial cells, respectively. SPRR2 is reported to selectively bind only buccal epithelial cells; thus, the binding efficacy was tested on both cells shed from the targeted buccal mucosa and breast epithelial cells to mimic what may be seen in oral-body sexual assault mixtures. Results from flow cytometry demonstrated that an average of 42.70%+30.33 of buccal epithelial cells were bound to the antibody, whereas only 1.204%+4.958 of breast epithelial cells in the gated population were bound by SPRR2 (p=0.0009) (not shown). Thus, the binding of SPRR2 is 36-fold higher for buccal cells than breast epithelial cells. These results suggest that SPRR2 effectively targets buccal mucosa, and is thus capable of differentiating between these buccal epithelial cells from skin.

The literature is contradictory about the location of SPRR2's target antigen in the buccal mucosa, as other publications state that it is found in the basal layer of buccal epithelium, which is the deepest portion of the tissue. In addition, the collection of buccal cells from one individual to another is variable, as one person may actively shed more cells than another. These factors may help explain why the antibody is only binding 42.70% of the buccal cells in the targeted population. Therefore, considering Cytokeratin 4 binds proportionately more buccal epithelial cells than SPRR2, its use may be preferred when differentiating between buccal and skin epithelial cells, such as those found within oral-body sexual assault samples.

Bead-Mediated Antibody Binding

Since both Cytokeratin 4 and SPRR2 demonstrated the ability to selectively bind the targeted cell type, the efficacy of bead-mediated antibody binding was tested for both antibodies in this category. This was performed by quantifying the amount of DNA liberated from cells that were bound and not bound to the beads in the targeted cell population. When using the Cytokeratin 4 bound polystyrene beads with buccal epithelial cells, an average of 76.46%+14.64 of the total DNA obtained was from cells bound to the beads, whereas 23.54%+14.94 of the total DNA was obtained from cells in the unbound fraction (p=0.0031). These data indicate that the Cytokeratin 4 antibody is capable of selectively binding to and enriching for buccal cells when binding is mediated by a polystyrene bead. When using SPRR2 bound polystyrene beads to target buccal epithelial cells, 38.17%+15.35 of the total DNA in the samples was in the bound fraction while 61.83%+15.35 was from cells in the unbound fraction (p=0.4044). Although this antibody did not efficiently bind a majority of the buccal cells, these results do correspond to those developed from flow cytometry. In addition, as stated above, the literature contains conflicting data regarding the location of SPRR2's target antigen on buccal epithelial cells.

Antibody Testing in a Plastic (PMMA) Microdevice

Since it was determined that the bead-mediated antibody binding is capable of selecting for and separating the targeted cell type (buccal epithelial cells) in this category, it was imperative to test and optimize this chemistry in a plastic (PMMA) microdevice with similar architecture as the sexual assault microdevice. When testing the Cytokeratin 4 bead-mediated mechanism using buccal epithelial cells, an average of 81.93%+13.55 total DNA was from the bound cell fraction and 18.07%+13.55 of the total DNA was from cells in the unbound fraction (p=0.0065) (FIG. 1 IA).

Figure 11A:
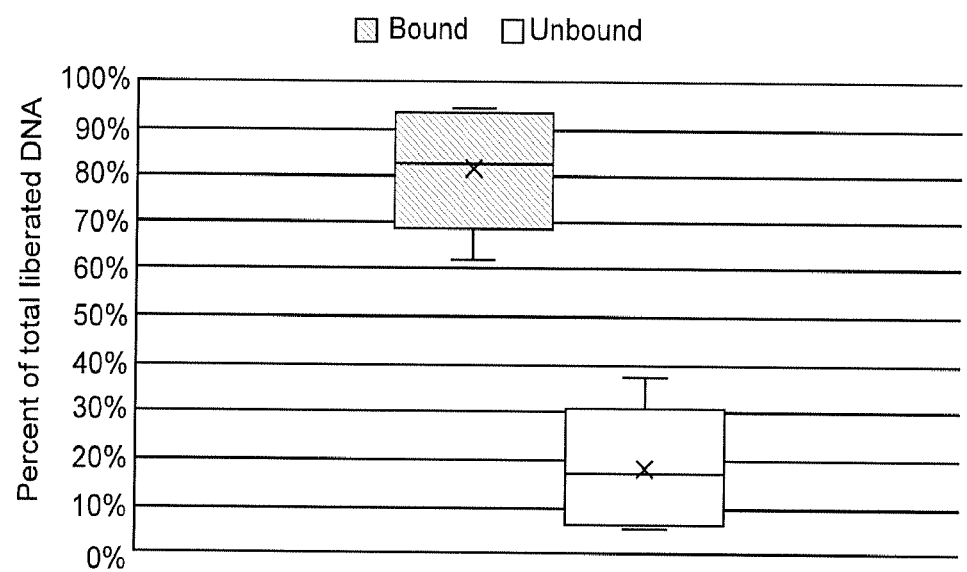
FIGS. 11A and B. A, Total liberated DNA in the bound and unbound fractions when using Cytokeratin 4-bound polystyrene beads to target buccal epithelial cells on a PMMA microdevice. The top and bottom of the box plots represent the first and third quartiles, respectively. The percent of the total DNA present in the bound fraction is significantly higher (p=0.0065) than the percent of the total DNA present in the unbound fraction (n=5);B, Total liberated DNA in the bound and unbound fractions when using SPRR2-bound polystyrene beads to target buccal epithelial cells on a PMMA microdevice. The percent of the total DNA present in the unbound fraction is significantly higher (p=0.0173) than the percent of the total DNA present in the bound fraction (n=5). For A and B, the middle line represents the median, the X represents the mean, and the whiskers extend to the maximum and minimum values in the dataset.
Figure 11B:
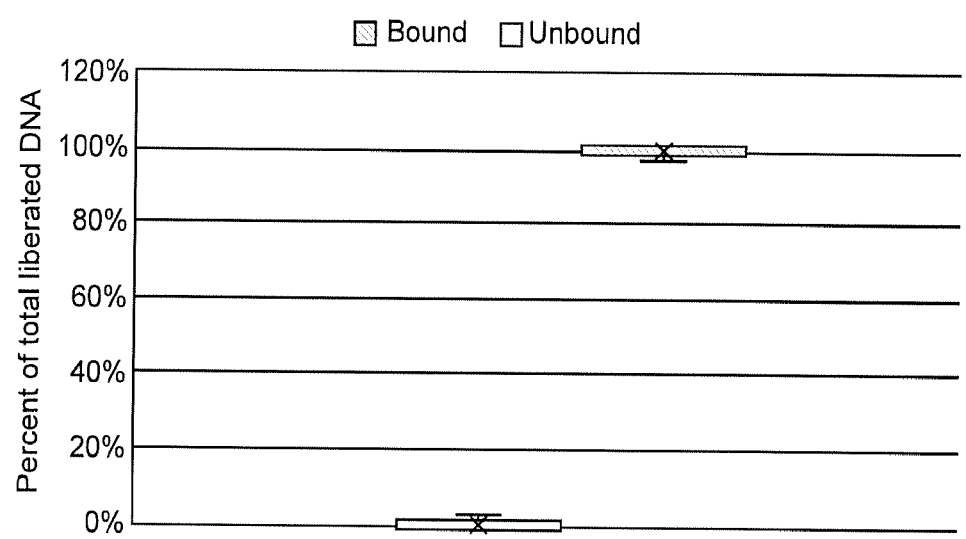

The next antibody-bead mechanism to test on the microdevice was SPRR2 using buccal epithelial cells. Unfortunately, when targeting the buccal epithelial cells, the percent of the total DNA from bound cells was 0.660%+1.480, whereas the percent of DNA from unbound cells was 99.34%+1.480 (p=0.0173) (FIG. 11B). The lack of DNA in the bound fraction is likely attributable to several variables. First, some reports in the literature identify the expression of this antibody to be on the suprabasal layer of the buccal mucosa (36); if true, then the target antigen would not be expressed on cells readily shed by buccal epithelia. Secondly, in the other tests performed, the antibody effectively bound only a small portion of the targeted cells, so when it is moved to a PMMA microdevice environment, the percent of total DNA from the bound cell fraction is expected to decrease (as was seen in the raw data of the other two antibodies tested also). Fortunately, Cytokeratin 4 has demonstrated its ability to selectively binds cells shed by buccal mucosa. As such, further testing on SPRR2 does not need to be performed. Cytokeratin 4 will be used for all subsequent testing of mixtures from mock oral-body sexual assault samples.

Penetration Without Semen

Flow Cytometry

Cytokeratin 4 selectively binds cells shed by all mucous membranes. Therefore, its binding efficacy was also tested against vaginal epithelial cells, as well as hand epithelial cells, as they are the presumed cell types in penetration without semen mixtures. On average, the targeted vaginal epithelial cells had significantly more positively stained cells (87.33%+4.391), than hand epithelial cells 13.50%+13.22. (p<0.0001).

This data, as well as the data generated from the oral-body assault testing, suggests that Cytokeratin 4 is capable of selectively binding to both buccal and vaginal epithelial cells and not shed epidermal cells, indicating that it can effectively differentiate between cells shed by a mucous membrane from keratinized epithelial cells. As such, this antibody would be suitable to use for both oral-body mixtures and penetration without semen mixtures from sexual assaults. However, it is present at similar concentrations on the surface of all stratified squamous epithelia, and would therefore not be capable of distinguishing between buccal and vaginal epithelial cells when both are present in an evidentiary sample.

Next, the binding efficacy of Laminin-1 was tested via flow cytometry with targeted cell types (vaginal and vulval epithelial cells) as well as with other cell types presumed present in non-sperm sexual assault mixtures (penile epithelial cells). Laminin-1 bound an average of 14.40%+11.35 of the targeted vulval cells and 30.68%+20.20 of the targeted vaginal cells, but only 5.256%+4.778 penile epithelial cells (p=0.0020).

Thus, Laminin-1 binding on vulval and vaginal epithelial cells was 3 and 6-fold higher than penile cells, respectively. The observed binding efficacy of vaginal and vulval epithelial cells is contradictory with the literature, which reports that the presence of Laminin-1 is increased in vulval epithelium and not vaginal epithelium. However, these results suggest that Laminin 1 can effectively differentiate between vaginal and penile epithelial cells. In addition, when both vaginal and vulval epithelial cells are present in an evidentiary sample, they can sufficiently be distinguished from penile epithelial cells.

Bead-Mediated Binding

When testing the binding efficacy of Cytokeratin 4-bound bead-mediated mechanism against vaginal epithelial cells, an average of 98.90%+1.270 total DNA was obtained from cells in the bound fraction, whereas only 1.900%+1.270 total DNA was present in cells from the unbound fraction (p=0.0001). When comparing the total DNA liberated from cells in the bound fractions for both targeted cell types (buccal and vaginal), the antibody-bead complex effectively bound more vaginal epithelial cells; however, this result was also demonstrated from flow cytometry. Laminin-1 bound polystyrene beads were also tested with both vaginal and vulval epithelial cells. For vaginal epithelial cells, 99.39%+0.5800 of the total DNA was present in the bound cell fraction and 0.6100%+0.5800 of total DNA in the samples was unbound (p=0.0315).

Next, when testing this complex using vulval epithelial cells, 61.88+53.71 of the total DNA was from the bound cell fraction and 38.12%+53.71 was from the unbound cell fraction (p=0.1554). The lack of difference noted between the two fractions from the vulval epithelial cells may be due the presence of outliers in the vulval bound fraction, which skewed the results. One factor likely contributing to these outliers is the variability in sampling, as it is difficult to assure standardized collection for this cell type. However, from these results, Laminin-1 shows promise for selectively binding vaginal epithelial cells when binding is mediated by a polystyrene bead. In addition, when targeting both cell types in a penetration without semen sexual assault sample, Laminin-1 can sufficiently bind and distinguish both vaginal epithelial and vulval epithelial cells from other cells present in sexual assault samples. Most importantly, the culmination of all the data from these tests for both sexual assault categories suggest that the antibody-bead complex is capable of effectively binding and separating the targeted cell type from other cells present in sexual assault samples.

Antibody Testing in a Plastic (PMMA) Microdevice

Figure 12A:
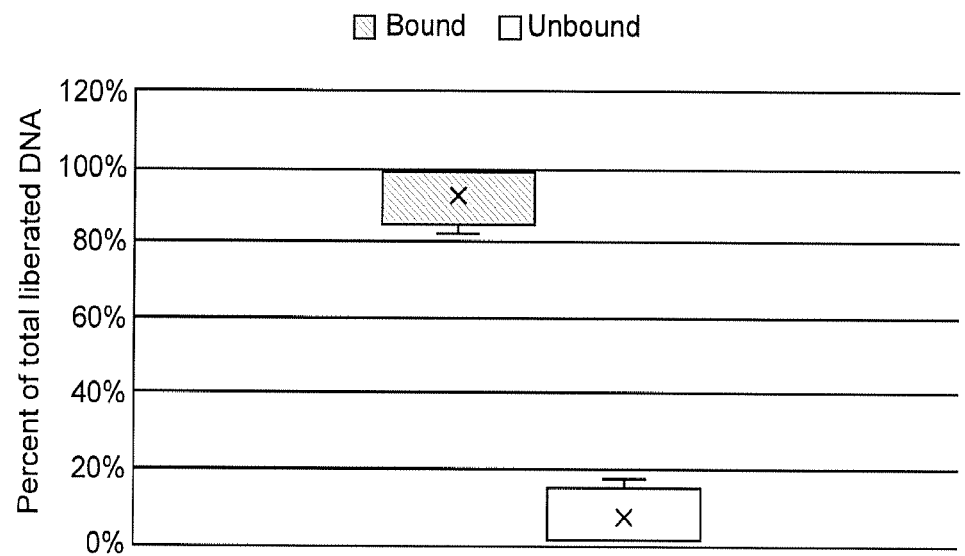
FIGS. 12A and B. A, Total liberated DNA in the bound and unbound fractions when using Cytokeratin 4-bound polystyrene beads to target vaginal epithelial cells on a PMMA microdevice. The top and bottom of the box plots represent the first and third quartiles, respectively. The percent of the total DNA present in the bound fraction is significantly higher (p=0.0072) than the percent of the total DNA present in the unbound fraction (n=5); B, Total liberated DNA present in the bound and unbound fractions vulval and vaginal epithelial cells with Laminin-1 bound polystyrene beads on a PMMA microdevice. The percent of total DNA in the vaginal bound fraction was significantly higher than the vaginal unbound fraction (p=0.0033); however, there was no significant difference in the percent of total DNA in the vulval bound and unbound fractions (p=0.9448) (n=3). For A and B, the middle line represents the median, the X represents the mean, and the whiskers extend to the maximum and minimum values in the dataset.

For the reasons listed in the oral-body assault category testing, the Cytokeratin 4-polystyrene bead complex was also tested with vaginal cell samples in a plastic (PMMA) microdevice. When evaluating the vaginal epithelial cell samples, 93.11%+7.560 of the total DNA was from the bound cell fraction, whereas 6.89%+7.560 of the total DNA in these samples was not bound (p=0.0072) (FIG. 12A). The consistency in the amount of DNA bound to the beads for both targeted cell types (buccal and vaginal) again suggests that Cytokeratin 4 is expressed on the surface of all cells shed by mucous membranes (36). In addition to the enrichment of both targeted cell types by the antibody-bead complexes, the data generated correlates with the values present in the flow cytometry and the bead-mediated testing. Therefore, Cytokeratin 4 is shown to be highly effective for targeting mucous membrane cells, and the antibody-bead complex can differentiate these cells from shed skin cells on a PMMA microdevice.

Figure 12B:
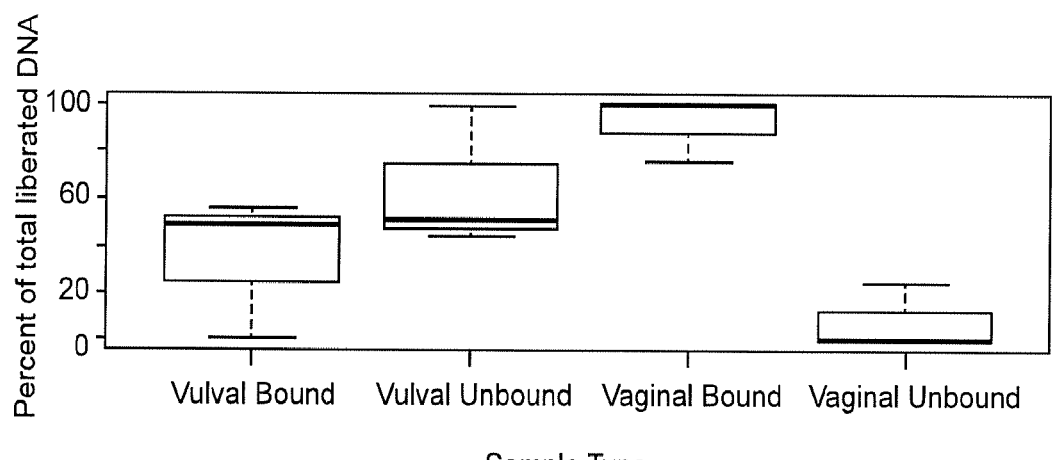

The Laminin-1 coated polystyrene bead complex was also tested on the PMMA microdevice with both vulval and vaginal epithelial cells. When targeting vulval epithelial cells, an average of 34.79%+30.29 of the total DNA in the samples was from cells bound to the beads and 65.21%+30.29 was from unbound cells (p=0.9448). In addition, when using this mechanism to target vaginal epithelial cells, 91.98%+13.60 of the total DNA from the sample was present in the bound cell fraction while 8.020%+13.60 was present in the unbound cell fraction (p=0.0033) (FIG. 12B). As such, this antibody-bead complex most successfully enriches for vaginal epithelial cells. Thus, although this complex does not enrich for vulval epithelial cells, it can selectively bind to both sample types, and because this data correlates with the previous results, three conclusions can be made. First, when using the Laminin 1 polystyrene bead complex, vaginal epithelial cells can be effectively bound and separated from other cell types in a mixed evidentiary sample. Secondly, if vulval epithelial cells are also present in the mixture, they are distinguishable; however, they are not as easily differentiated from shed epidermal cells such as penile epithelial cells, as was seen in the flow cytometry data. Lastly, the Laminin-1 polystyrene bead complex can selectively bind these samples in a plastic (PMMA) microdevice environment and thus should be tested using mixtures from mock sexual assault samples that reflect penetration without semen.

Cell Separation Testing in the Sexual Assault Microdevice

The final step of this work was to test the antibody-bead complex within the separation module architecture as designed in the assault microdevice. Since the SPRR2 complex did not enrich for buccal cells in the bound fraction, it was not moved to this stage of testing. However, both Cytokeratin 4 and Laminin-1 were capable of selectively binding the targeted cell type in all three studies, and were therefore moved to testing on the sexual assault microdevice.

The Cytokeratin 4 bead complex alone is tested using six different scenarios: neat buccal samples, neat vaginal samples, neat breast samples, neat penile samples, mixture samples containing buccal and breast epithelial cells (oral-body assault), and mixture samples containing vaginal and penile epithelial cells (penetration without semen). Next, the Laminin-1 bead complex is tested using five different scenarios: neat vaginal samples, neat penile samples, mixture samples that contained vaginal and penile epithelial cells (penetration without semen), neat vulval samples, and mixture samples that contained vulval and penile epithelial cells (penetration without semen sexual assaults).

The last test in this study uses a combination of Cytokeratin 4 and Laminin-1 bead complexes for increased enrichment for vaginal cells (bound fraction) to more accurately and effectively separate them from skin cells that may be present in sexual assault mixture samples.

Conclusions

Results from these studies demonstrate that Cytokeratin 4 is able to effectively bind targeted mucosal epithelial cells (shed by vaginal and buccal mucosa) and differentiate them from skin cells that may be present in a mixture. In addition, when binding is mediated by polystyrene beads, its high efficiency is maintained and shown to be successful even in a plastic (PMMA) microdevice environment. Laminin-1 was purported to be expressed on the surface of vulval epithelial cells; however, this study concludes that it is more selective for vaginal epithelial cells. In addition, it is able to efficiently distinguish between vaginal and penile epithelial cells that may be present in a sexual assault sample. When testing the Laminin-1 bound polystyrene bead complex in the microcentrifuge tube and on the simple microdevice, the vaginal epithelial cells were enriched by the antibody-bead complex, but the vulval epithelial cells were not. This antibody shows promise for differentiating between vaginal epithelial cells from other cell types (skin cells) that may be present in sexual assault samples.

Lastly, SPRR2 is solely expressed on the surface of buccal epithelial cells; however, the literature data regarding its location on the buccal mucosa is contradictory and, our studies show that although this antibody does selectively bind buccal epithelial cells in the targeted population, it is not capable of doing so when bound to polystyrene beads. Since the SPRR2 bead complex did not enrich for buccal cells in the microcentrifuge and simple microdevice, this antibody is not able to reliably distinguish buccal epithelial cells from other cells present in a sexual assault sample.

The results from these studies have identified two antibodies, Cytokeratin 4 and Laminin-1, that can effectively bind target cells for successful differentiation from other cell types present in sexual assault mixtures. With the incorporation of these antibodies, this sexual assault microdevice shows promise for the separation of cells shed by different tissues present in sexual assault samples. This microdevice is capable of decreasing the amount of time needed for sample processing while also minimizing the need for difficult mixture interpretations. The modular microdevice is advantageously designed for various sample types, it is portable, it decreases the amount of manual manipulation, and it is inexpensive.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A microfluidic device for processing sexual assault samples, comprising
a sample-input chamber configured for separating a biological sample containing a plurality of cells of multiple cell types from a sample collection device;
an on-chip differential separating chamber downstream of the sample-input chamber, the on-chip differential separating chamber being configured to receive the biological sample containing the plurality of cells of multiple cell types;

a plurality of capture molecules affixed to a substrate, wherein the plurality of capture molecules are anti-sperm antibodies, wherein the plurality of capture molecules and the substrate are all arranged in the same on-chip differential separating chamber, wherein the on-chip differential separating chamber accommodates combining of the plurality of cells of multiple cell types with the plurality of capture molecules, wherein the plurality of capture molecules are capable of sequestering in the on-chip differential separating chamber a plurality of cells of a first cell type of interest and no cells of other cell types besides the first cell type from the biological sample; and at least one microvalve openable during application of a centrifugal force, wherein the at least one microvalve is configured
- to prevent egress of the plurality of capture molecules affixed to the substrate and any cells sequestered by the plurality of capture molecules, and
- to allow egress of at least some components of the biological sample which are unsequestered by the plurality of capture molecules, including the other cell types besides the first cell type;

a lysis chamber downstream of the microvalve and configured for combining a lysis solution with the at least some components of the biological sample which are unsequestered by the plurality of capture molecules, wherein the on-chip differential separating chamber is configured to receive and contain a separate lysis solution;

a first metering chamber downstream from the on-chip differential separating chamber;

a second metering chamber downstream from both the on-chip differential separating chamber and the lysis chamber, wherein the first and second metering chambers are parallel circuit elements with respect to one another;

a second valve configured to allow passage of cellular components comprising DNA but not the substrate from the on-chip differential separating chamber to the first metering chamber when opened.

2. The microfluidic device of claim 1, wherein the at least one microvalve is a laser "tap" valve.

3. The microfluidic device of claim 1, wherein the configuration of the microvalve to perform selective prevention and allowance of egress is on the basis of size, wherein a smaller size of the microvalve as compared to the substrate prevents egress of the substrate.

4. The microfluidic device of claim 1, further comprising
a first storage chamber downstream of the first metering chamber;
a second storage chamber downstream of the second metering chamber;
a first reagent mixing chamber downstream of the first metering chamber and in parallel with the first storage chamber; and
a second reagent mixing chamber downstream of the second metering chamber and in parallel with the second storage chamber.

5. The microfluidic device of claim 4, further comprising a first heatable polymerase chain reaction (PCR) chamber and a second heatable PCR chamber downstream from the first mixing chamber and the second mixing chamber, respectively, configured for combining cellular materials and PCR reagents.

6. The microfluidic device of claim 5, wherein the first and second metering chambers are connected to the first and second heatable PCR chambers, respectively, via a first serpentine mixing channel and a second serpentine mixing channel, respectively.

7. The microfluidic device of claim 5, further comprising one or more channels which allow access to one or more of the on-chip differential separating chamber, the lysis chamber, the first metering chamber, the second metering chamber, the first storage chamber, the second storage chamber, the first heatable PCR chamber and the second heatable PCR chamber.

8. The microfluidic device of claim 5, further comprising a PCR reference chamber.

9. The microfluidic device of claim 8, wherein the PCR reference chamber comprises a thermocouple.

10. A rotational microfluidic platform system, comprising:
a microfluidic device as set forth in claim 1,
a heater,
a cooler,
a centrifugal force (CF) source, wherein the microfluidic device is attachable to the CF source.

11. The rotational microfluidic platform system of claim 10, wherein the heater is a Peltier heater.

12. The rotational microfluidic platform system of claim 10, wherein the cooler is a fan.

13. The rotational microfluidic platform system of claim 10, wherein the CF source is a centrifuge platform.

14. The rotational microfluidic platform system of claim 10, further comprising a controller configured to control the heater, cooler, and CF source.

15. The rotational microfluidic platform system of claim 14, wherein the controller comprises one or more computers.

16. A microfluidic device for processing sexual assault samples, comprising
I. a first chamber for receiving a biological sample containing a plurality of cells of multiple cell types;
II. a second chamber configured to receive the biological sample from the first chamber, wherein
  i) the second chamber comprises a plurality of capture molecules capable of sequestering in the second chamber a plurality of cells of a first cell type of interest and no cells of other cell types besides the first cell type from the biological sample, the plurality of capture molecules being affixed to a substrate, wherein the plurality of capture molecules and the substrate are all arranged in the same second chamber, wherein the second chamber accommodates combining of the plurality of cells of multiple cell types with the plurality of capture molecules, wherein the plurality of capture molecules are anti-sperm antibodies;
  ii) the second chamber comprises a first burst valve openable upon application of centrifugal force to the microdevice, wherein a size of the first burst valve allows sample components to egress the second chamber and enter a third chamber configured to receive and contain a lysis solution, but is insufficient to allow the capture molecule affixed to the substrate to pass through; and
  iii) the second chamber is configured to receive and contain a lysis solution;
III. a first metering chamber configured to receive cellular components comprising DNA from the second chamber and a second metering chamber configured to receive cellular components from the third chamber, wherein the first and second metering chambers are configured to
a. release a first portion of the cellular components to a first storage chamber and a second storage chamber, respectively, via a mechanical valve; and
b. release a second portion of the cellular components to a first mixing chamber and a second mixing chamber, respectively, via a second burst valve openable upon application of centrifugal force to the microdevice; and IV. a first PCR chamber and a second PCR chamber configured to receive and contain cellular material from the first mixing chamber and the second mixing chamber, respectively, and PCR reagents.

* * * * *